(12) United States Patent
Tamm et al.

(10) Patent No.: US 7,655,634 B2
(45) Date of Patent: Feb. 2, 2010

(54) USE OF HEPATITIS B X-INTERACTING PROTEIN (HBXIP) IN MODULATION OF APOPTOSIS

(75) Inventors: Ingo Tamm, Berlin (DE); John C. Reed, Rancho Santa Fe, CA (US)

(73) Assignee: The Burnham Institute, La Jolla, CA (US)

( * ) Notice: Subject to any disclaimer, the term of this patent is extended or adjusted under 35 U.S.C. 154(b) by 99 days.

(21) Appl. No.: 11/691,393

(22) Filed: Mar. 26, 2007

(65) Prior Publication Data
US 2007/0270369 A1    Nov. 22, 2007

Related U.S. Application Data

(62) Division of application No. 10/665,975, filed on Sep. 18, 2003, now abandoned.

(60) Provisional application No. 60/412,109, filed on Sep. 18, 2002.

(51) Int. Cl.
 C07H 21/02 (2006.01)
 C07H 21/04 (2006.01)
 A61K 31/70 (2006.01)
 C12Q 1/68 (2006.01)
 C12N 5/00 (2006.01)

(52) U.S. Cl. ........................ 514/44; 536/23.1; 536/24.1; 536/24.5; 435/6; 435/375; 435/377

(58) Field of Classification Search ........................ None
See application file for complete search history.

(56) References Cited

U.S. PATENT DOCUMENTS

| | | | |
|---|---|---|---|
| 6,838,283 B2 * | 1/2005 | Bennett et al. | 435/375 |
| 2003/0206887 A1 * | 11/2003 | Morrissey et al. | 424/93.2 |
| 2004/0072170 A1 * | 4/2004 | Bunk et al. | 435/6 |
| 2004/0259247 A1 * | 12/2004 | Tuschl et al. | 435/375 |

OTHER PUBLICATIONS

Ambrosini, G. et al. "A novel anti-apoptosis gene, *survivin*, expressed in cancer and lymphoma." *Nature Med* 3:917-921 (1997).
Banks, D.P. et al. "Survivin does not inhibit caspase-3 activity." *Blood* 96:4002-4003 (2000).
Bratton, S.B. et al. "Recruitment, activation and retention of caspases-9 and -3 by Apaf-1 apoptosome and associated XIAP complexes."*EMBO J* 20:998-1009 (2001).
Cryns, V. et al. "Proteases to die for."*Genes Dev* 12:1551-1570 (1998).
Deveraux, Q.L. et al. "IAP family proteins: Suppressors of apoptosis. "*Genes Dev* 13:239-252 (1999).
Deveraux, Q.L. et al. "X-linked IAP is a direct inhibitor of cell death proteases." *Nature* 388:300-304 (1997).

Gottlob, K. et al. "The Hepatitis B virus HBx protein inhibits caspase 3 activity."*J Biol Chem* 273:33347-33353 (1998).
Grossman, D. et al. "Transgenic expression of survivin in keratinocytes counteracts UVB-induced apoptosis and cooperates with loss of p53."*J Clin.Invest* 108:991-999 (2001).
Kim, C.M. et al. "HBx gene of hepatitis B virus induces liver cancer in transgenic mice. "*Nature* 351:317-320 (1991).
Li, F. et al. "Control of apoptosis and mitotic spindle checkpoint by survivin." *Nature* 396:580-584 (1998).
Li, P. et al. "Cytochrome c and dATP-dependent formation of Apaf-1/Caspase-9 complex initiates an apoptotic protease cascade." *Cell* 91:479-489 (1997).
Lok, A.S. "Hepatitis B infection: Pathogenesis and management." *J Hepatol* 32:89-97 (2000).
Marusawa, H. et al. "HBXIP functions as a cofactor of survivin in apoptosis suppression" *The EMBO J.* 22:2729-2740 (2003).
Marusawa, H. et al. "Latent hepatitis B virus infection in healthy individuals with antibodies to hepatitis B core antigen." *Hepatology* 31:488-495 (2000).
Matsuzawa, S. et al. "Siah-1, SIP, and Ebi collaborate in a novel pathway for -catenin degradation linked to p53 responses." *Mol Cell* 7:915-926 (2001).
Melegari, M. et al. "Cloning and characterization of a novel hepatitis B virus x binding protein that inhibits viral replication." *J Virol* 72:1737-1743 (1998).
Murakami S. "Hepatitis B virus X protein: A multifunctional viral regulator." *J Gastroenterol* 36:651-660 (2001).
O'Connor, D.S. et al. "Regulation of apoptosis at cell division by p34$^{cdc2}$ phosphorylation of survivin." *PNAS USA* 97:13103-13107 (2000).
Reed, J.C. et al. "BIRinging chromosomes through cell division—and survivin the experience." *Cell* 102: 545-548 (2000).
Reed, J.C. "The survivin saga goes in vivo." *J Clin Invest* 108:965-969 (2001).
Riedl, S.J. et al. "Structural basis for the inhibition of caspase-3 by XIAP." *Cell* 104:791-800 (2001).
Salvesen, G.S. "Caspases: opening the boxes and interpreting the arrows." *Cell Death Differ* 9:3-5 (2002).
Shin, S. et al. "An anti-apoptotic protein human survivin is a direct inhibitor of caspase-3 and -7." *Biochem* 40: 1117-1123 (2001).
Stennicke, H.R. et al. "Caspase-9 can be activated without proteolytic processing." *J Biol Chem* 274:8359-8362 (1999).
Sun, C. et al. "NMR structure and mutagenesis of the inhibitor-of-apoptosis protein XIAP." *Nature* 401:818-822 (1999).
Tamm, I. et al. "IAP-family protein survivin inhibits caspase activity and apoptosis induced by Fas (CD95), Bax, caspases, and anticancer drugs." *Cancer Res* 58:5315-5320 (1998).
Yagihashi, A. et al. "Detection of anti-survivin antibody in gastrointestinal cancer patients" Clin. Chem. 47 :1729-1731 (2001).
Velculescu, V.E. et al. "Analysis of human transcriptomes." *Nature Gen* 23:387-388 (1999).

(Continued)

*Primary Examiner*—Sean R McGarry
(74) *Attorney, Agent, or Firm*—DLA Piper LLP (US)

(57) ABSTRACT

Novel methods of regulating cellular apoptosis by affecting the interaction of hepatitis B X-interacting protein (HBXIP) with Survivin are described. More specifically, these novel methods of enhancing apoptosis of neoplastic cells comprises inhibiting interaction of hepatitis B X-interacting protein (HBXIP) with Survivin using siRNA or antisense compounds.

22 Claims, 7 Drawing Sheets

OTHER PUBLICATIONS

Verdecia, M.A. et al. "Structure of the Human anti-apoptotic protein survivin reveals a dimeric arrangement." *Nature Struct Biol* 7:602-608 (2000).

Yang, J. et al. "Prevention of apoptosis by Bcl-2: release of cytochrome c from mitochondria blocked." *Science* 275: 1129-1132 (1997).

Zhou, Q. et al. "Target protease specificity of the viral serpin CrmA: analysis of five caspases." *J Biol Chem* 272: 7797-7800 (1997).

Zou, H. et al. "An APAF-1 cytochrome c multimeric complex is a functional apoptosome that activates procaspase-9." *J Biol Chem* 274:11549-11556 (1999).

* cited by examiner

SEQUENCE LISTING

<160> NUMBER OF SEQ ID NOS: 8

<210> SEQ ID NO 1
<211> LENGTH: 429
<212> TYPE: DNA
<213> ORGANISM: Homo sapiens

<400> SEQUENCE: 1

```
atgggtgccc cgacgttgcc ccctgcctgg cagcccttc  tcaaggacca ccgcatctct      60
acattcaaga actggccctt cttggagggc tgcgcctgca ccccggagcg gatggccgag     120
gctggcttca tccactgccc cactgagaac gagccagact tggcccagtg tttcttctgc     180
ttcaaggagc tggaaggctg ggagccagat gacgacccca tagaggaaca taaaaagcat     240
tcgtccggtt gcgctttcct ttctgtcaag aagcagtttg aagaattaac ccttggtgaa     300
tttttgaaac tggacagaga aagagccaag aacaaaattg caaaggaaac caacaataag     360
aagaaagaat ttgaggaaac tgcgaagaaa gtgcgccgtg ccatcgagca gctggctgcc     420
atggattga                                                             429
```

<210> SEQ ID NO 2
<211> LENGTH: 142
<212> TYPE: PRT
<213> ORGANISM: Homo sapiens

<400> SEQUENCE: 2

```
Met Gly Ala Pro Thr Leu Pro Pro Ala Trp Gln Pro Phe Leu Lys Asp
 1               5                  10                  15

His Arg Ile Ser Thr Phe Lys Asn Trp Pro Phe Leu Glu Gly Cys Ala
```

```
                20                  25                  30
Cys Thr Pro Glu Arg Met Ala Glu Ala Gly Phe Ile His Cys Pro Thr
            35                  40                  45

Glu Asn Glu Pro Asp Leu Ala Gln Cys Phe Phe Cys Phe Lys Glu Leu
 50                  55                  60

Glu Gly Trp Glu Pro Asp Asp Pro Ile Glu His Lys Lys His
 65                  70                  75                  80

Ser Ser Gly Cys Ala Phe Leu Ser Val Lys Gln Phe Glu Glu Leu
                 85                  90                  95

Thr Leu Gly Glu Phe Leu Lys Leu Asp Arg Gly Arg Ala Lys Asn Lys
             100                 105                 110

Ile Ala Lys Glu Thr Asn Asn Lys Lys Lys Glu Phe Glu Thr Ala
         115                 120                 125

Lys Lys Val Arg Arg Ala Ile Glu Gln Leu Ala Ala Met Asp
 130                 135                 140
```

<210> SEQ ID NO 3
<211> LENGTH: 276
<212> TYPE: DNA
<213> ORGANISM: Homo sapiens

<400> SEQUENCE: 3

```
atggaggcga ccttggagca gcacttggaa gacacaatga agaatccctc cattgttgga    60
gtcctgtgca cagattcaca aggacttaat ctgggttgcc gcgggaccct gtcagatgag   120
catgctggag tgatatctgt tctagcccag caagcagcta agctaacctc tgaccccact   180
gatattcctg tggtgtgtct agaatcagat aatgggaaca ttatgatcca gaaacacgat   240
ggcatcacgg tggcagtgca caaaatggcc tcttga                            276
```

<210> SEQ ID NO 4
<211> LENGTH: 91
<212> TYPE: PRT
<213> ORGANISM: Homo sapiens

<400> SEQUENCE: 4

```
Met Glu Ala Thr Leu Glu Gln His Leu Glu Asp Thr Met Lys Asn Pro
 1               5                  10                  15

Ser Ile Val Gly Val Leu Cys Thr Asp Ser Gln Gly Leu Asn Leu Gly
             20                  25                  30

Cys Arg Gly Thr Leu Ser Asp Glu His Ala Gly Val Ile Ser Val Leu
         35                  40                  45

Ala Gln Gln Ala Ala Lys Leu Thr Ser Asp Pro Thr Asp Ile Pro Val
     50                  55                  60

Val Cys Leu Glu Ser Asp Asn Gly Asn Ile Met Ile Gln Lys His Asp
 65                  70                  75                  80

Gly Ile Thr Val Ala Val His Lys Met Ala Ser
                 85                  90
```

<210> SEQ ID NO 5
<211> LENGTH: 29
<212> TYPE: DNA
<213> ORGANISM: Artificial Sequence
<220> FEATURE:
<223> OTHER INFORMATION: forward oligonucleotide primer

<400> SEQUENCE: 5

```
gacgaattca tggaggcgac cttggagca                                      29
```

```
<210> SEQ ID NO 6
<211> LENGTH: 29
<212> TYPE: DNA
<213> ORGANISM: Artificial Sequence
<220> FEATURE:
<223> OTHER INFORMATION: reverse oligonucleotide primer

<400> SEQUENCE: 6
gatctcgagt caagaggcca ttttgtgca                                     29

<210> SEQ ID NO 7
<211> LENGTH: 21
<212> TYPE: DNA
<213> ORGANISM: Artificial Sequence
<220> FEATURE:
<223> OTHER INFORMATION: sense RNA oligonucleotide

<400> SEQUENCE: 7
gcagcuaagc uaaccucugt t                                             21

<210> SEQ ID NO 8
<211> LENGTH: 21
<212> TYPE: DNA
<213> ORGANISM: Artificial Sequence
<220> FEATURE:
<223> OTHER INFORMATION: antisense RNA oligonucleotide

<400> SEQUENCE: 8
ttcgucgauu cgauuggaga c                                             21
```

USE OF HEPATITIS B X-INTERACTING PROTEIN (HBXIP) IN MODULATION OF APOPTOSIS

RELATED APPLICATIONS

This application is a divisional application of U.S. application Ser. No. 10/665,975 filed on Sep. 18, 2003, which claims the benefit of priority under 35 U.S.C. 119(e) of the U.S. Provisional Application 60/412,109 filed Sep. 18, 2002, the disclosures of which are expressly incorporated herein by reference in its entirety.

GOVERNMENTAL INTEREST

This invention was made with government support under grant number AG15343 awarded by the National Institutes of Health. The United States Government may have certain rights in this invention.

FIELD OF THE INVENTION

The present invention is related to regulation of apoptosis. More specifically the present invention is related to the use of hepatitis B X-interacting protein (HBXIP) in the stimulation of apoptosis in neoplastic diseases.

BACKGROUND OF THE INVENTION

Survivin represents one of the most tumor-specific genes in the human genome according to comparisons of the transcriptomes of normal and malignant cells (Velculescu, V. E. et al. 1999 *Nature Gen* 23:387-388). The 17 kDa protein Survivin is scarcely expressed in normal adult tissues, but is found at high levels in most human cancers (Ambrosini, G. et al. 1997 *Nature Med* 3:917-921). Normally, Survivin is expressed only during late stages of the cell cycle (particularly mitosis and anaphase), where it associates with the mitotic spindle and related structures, performing functions important for chromosome segregation and cytokinesis (Li, F. et al. 1998 *Nature* 396:580-587; Reed, J. C. & Bischoff, J. R. 2000 *Cell* 102:545-548). Many cancers, however, contain constitutively high levels of cytosolic p17 Survivin, and over-expression of this protein has been shown to block apoptosis both in vitro in cultured cells and in vivo in transgenic mice (Ambrosini, G. et al. 1997 *Nature Med* 3:917-921; Grossman, D. et al. 2001 *J Invest* 108:991-999; Reed, J. C. 2001 *J Clin Invest* 108:965-969). Antisense and dominant-negative experiments have provided proof of concept evidence suggesting that interfering with Survivin function could be a worthwhile strategy for promoting apoptosis of tumor cells (Reed, J. C. 2001 *J Clin Invest* 108:965-969; Li, F. et al. 1999 *Nature Cell Biol* 1:461-466; Mesri, M., et al. 2001 *J Clin Invest* 108:981-990). However, at present it is unclear how Survivin blocks apoptosis.

Survivin is a member of a family of proteins which all contain a characteristic zinc-binding fold called the BIR domain. Many of these BIR-containing proteins have been shown to suppress apoptosis when over-expressed, thus prompting the term Inhibitor of Apoptosis Proteins (IAPs). The principal mechanism of apoptosis suppression by IAP-family members such as XIAP has been defined. These proteins directly bind and potently suppress the activity of Caspases (Deveraux, Q. L. & Reed, J. C. 1999 *Genes Dev* 13:239-252), a group of intracellular proteases responsible for apoptosis (reviewed in Cryns, V. & Yuan, Y. 1999 *Genes Dev* 12:1551-1570). Though some studies have suggested that p17 Survivin also binds and suppresses Caspases, others have failed to demonstrate direct effects on these proteases (Shin, S. et al. 2001 *Biochem* 40:1117-1123; Verdecia, M. A. et al. 2000 *Nature Struct Biol* 7:602-608; Conway, E. M. et al. 2000 *Blood* 95:1435-1442; Banks, D. P. et al. 2000 *Blood* 96:4002-4003).

Because Survivin is over-expressed in the majority of tumors (Velculescu, V. E. et al. 1999 *Nature Gen* 23:387-388; Ambrosini, (G. et al. 1997 *Nature Med* 3:917-921), this protein has emerged as a promising target for development of new cancer therapies. However, progress in devising strategies for nullifying Survivin has been hampered by a lack of knowledge about its biochemical mechanism of action.

HBXIP was originally isolated as a human protein which binds the viral oncogenic protein, HBX, of the Hepatitis B Virus (HBV) (Melegari, M. et al. 1998 *J Virol* 72:1737-1743). HBXIP encodes a protein of 9.6-kDa with a putative leucine zipper motif. Expression of HBXIP mRNA has been demonstrated in essentially all tissues examined to date, and is not limited to the liver (Melegari, M. et al. 1998 *J Virol* 72:1737-1743). In the context of HBV-infection, HBXIP reportedly reduces viral replication and abolishes the transactivation function of viral HBX protein (Melegari, M. et al. 1998 *J Virol* 72:1737-1743), however, little is known about the physiological roles of HBXIP in human cells.

Thus, there is a need for investigation into the anti-apoptotic mechanism of Survivin and its role in neoplastic diseases as a means for developing novel cancer treatments.

SUMMARY OF THE INVENTION

In one embodiment, the present invention includes a method for regulating cellular apoptosis by affecting interaction of hepatitis B X-interacting protein (HBXIP) with Survivin. A method for enhancing apoptosis of neoplastic cells is described, wherein interaction of hepatitis B X-interacting protein (HBXIP) with Survivin is inhibited. SiRNA or antisense can be used to downregulate expression of HBXIP. The level of HBXIP can also be reduced in the presence of HBXIP- or Survivin-specific antibodies. In yet another embodiment, the interaction of HBXIP with Survivin may be inhibited with the use of specific inhibitors, molecular decoys, or the like.

Another aspect of the invention includes a pharmaceutical composition comprising a compound that inhibits HBXIP in the presence of Survivin. Yet another embodiment is a method of treating neoplastic disease comprising administration of an inhibitor of HBXIP in the presence of Survivin. A method for treating human liver disease associated with HBV is also described, comprising administration of an inhibitor of HBXIP in the presence of Survivin.

BRIEF DESCRIPTION OF THE DRAWINGS

In FIGS. 1*a* and 1*b*, 100 µM recombinant active Caspase-3 was incubated with recombinant Survivin (FIG. 1*a*) or XIAP (FIG. 1*b*) or with control protein. In FIGS. 1*c* and 1*d*, purified Survivin (FIG. 1*c*) or XIAP (FIG. 1*d*), or control protein was added concurrently with the addition of Cytochrome C and dATP. In FIGS. 1*e* and 1*f*, Survivin (FIG. 1*e*) or XIAP (FIG. 1*f*) was added after stimulation with Cytochrome c and dATP. Caspase activity was continuously measured, and results are shown in RFU, relative fluorescence units.

FIG. 2*a* shows the results of in vitro binding experiments. FIGS. 2*b* and 2*c* show gel-sieve chromatography and FIG. 2*d* shows Scatchard analysis of His$_6$-HBXIP binding to purified Survivin (untagged). (B, bound Survivin; F, free Survivin). FIG. 2*e* shows the results of mapping of region in Survivin required for binding HBXIP, autoradiography. FIG. 2*f* shows the results of immunoblotting using anti-myc antibody (upper panel), anti-myc (middle panel) or anti-FLAG antibodies (lower panel). FIG. 2*g* shows the results of immunoblotting of lysates from untransfected HepG2 cells prepared for immunoprecipitation with anti-Survivin antisera with anti-HBXIP or anti-Survivin antibodies. FIG. 2*h* shows the results of immunoblotting of subcellular fractionation of 293 cells (M, membrane; C, cytoplasmic; N, nuclear) using anti-HBXIP and anti-Survivin antibodies.

FIGS. 3*a*-3*c* show the effects of purified HBXIP and Survivin on Caspase activity induced by Cytochrome C (FIG. 3*a*), Caspase-8 (FIG. 3*b*) or Granzyme B (FIG. 3*c*), measured as AFC release from Ac-DEVD-AFC in cell extracts. His$_6$-HBXIP, Survivin (SVV), or the combination of these proteins was added to 293 cell lysates prior to Cytochrome c (and dATP), recombinant active Caspase-8, or Granzyme B. CTR, control proteins tested. FIGS. 3*d* and 3*e* illustrate the effects of recombinant HBXIP, Survivin, or the combination of these proteins or various control (CTR) proteins on Caspase-9 activity measured by the cleavage of fluorogenic substrate Ac-LEHD-AFC (FIG. 3*d*) or proteolytic processing of ~50 kDa pro-Caspase-9 to ~35 kDa large and ~12 kDa small subunits, analyzed by immunoblotting analysis using anti-Caspase-9 antibody (FIG. 3*e*). Minus-signs indicate addition of an equivalent amount of a control protein (GST-CD40 or His$_6$-Traf3) instead of Survivin or His$_6$-HBXIP.

FIG. 4*a* illustrates the results of immunoblotting using GST-Survivin, GST-CD40 or GST-HBXIP with or without purified Survivin (untagged), incubated with His$_6$-pro-Caspase-9, active His$_6$-Caspase-9 (lacking CARD domain) or His$_6$-pro-Caspase-3. GST-fusion proteins were recovered using glutathione-Sepharose and bound proteins were detected by immunoblotting using anti-Caspase-9 or anti-Caspase-3 antisera. An equivalent amount of proteins was loaded directly in gels as a control ("input"). FIG. 4*b* shows the results when $^{35}$S-labeled pro-Caspase-9 was incubated with His$_6$-Apaf1, Cytochrome C and dATP, in the absence or presence of GST-HBXIP and Survivin. His$_6$-Apaf1 and associated proteins were recovered by adsorption to Ni-resin, and bound proteins were analyzed by autoradiography (for Caspase-9) or immunoblotting using anti-Apaf1 or anti-Cytochrome C antibodies. FIGS. 4*c* and 4*d* illustrate the results when purified His$_6$-Apaf1, His$_6$-pro-Caspase-9, Cytochrome C and dATP were incubated in the absence (FIG. 4*c*) or presence (FIG. 4*d*) of recombinant purified Survivin and HBXIP. Proteins were analyzed by gel-sieve chromatography, using immunoblotting to detect proteins in eluted fractions. FIG. 4*e* shows caspase activity in column fractions from gel-sieve experiments, determined by monitoring the cleavage of Ac-DEVD-AFC after the incubation of each fraction from FIG. 4*c* and FIG. 4*d* with recombinant pro-Caspase-3. FIG. 4*f*: (Upper panel) Full-length purified GST-HBXIP and GST-HBXIP (1-40) tested for binding to His$_6$-Survivin or control protein (His$_6$-Traf3). Bound proteins were analyzed by immunoblotting using anti-GST antisera (upper panel). An equivalent amount of GST-fusion protein was loaded directly in gels as a control ("input"). (Lower panel) HT1080 cells were transiently transfected with expression plasmids encoding myc-Survivin, FLAG-HBXIP, FLAG-HBXIP(1-40), Bcl-XL (for Staurosporine [STS]), or CrnA (for anti-Fas), alone or in various combinations, with pEGFP marker plasmid, using pcDNA3 to normalize total DNA content. Then, cells were cultured with STS or anti-Fas antibody, and the percentage of apoptotic cells was determined by DAPI staining (mean±SE; n=3) one day later.

FIG. 5*a* shows that HBXIP expression is elevated in HBV-infected liver and hepatocellular cancers. Protein samples from the tumors (T) and non-malignant tissue (NT) of three patients with HBV-related-hepatocellular carcinoma and two normal livers specimens (N1 and N2) analyzed by SDS-PAGE/immunoblotting using antisera specific for HBXIP, Survivin or d-Tubulin (as a control). FIG. 5*b* illustrates caspase activity in the same tissue samples measured using fluorigenic substrate Ac-DEVD-AFC after treatment with Cytochrome c and dATP (left panel) or with Granzyme B (right panel). Results are arbitrarily expressed relative to Caspase activity generated in normal liver specimen (N1) (mean±SE; n=3 determinations). FIG. 5*c* illustrates immunoblotting analysis of HeLa cells transfected with siRNA targeting HBXIP or control RNA (CTR), using anti-HBXIP and anti-α-Tubulin (loading control) antisera. FIG. 5*d* shows caspase activity in HeLa cell extracts after treatment with HBXIP-siRNA or control-RNA and incubation with Cytochrome C and dATP, in the presence or absence recombinant Survivin (left panel) or XIAP (right panel), measured as a release of AFC from Ac-DEVD-AFC substrate (mean±SE; n=3). FIG. 5*e* shows the percentage of apoptotic cells (mean±SE; n=3) determined by DAPI-staining following culture of control-RNA- or HBXIP siRNA-transfected HeLa cells with Etoposide (VP-16) or Staurosporine (STS).

FIG. 6*a* shows immunoblot analysis using anti-HBX antibody of in vitro protein binding after incubation of recombinant His$_6$-HBX with GST-HBXIP, GST-Survivin, or GST-CD40 (control). FIGS. 6*b* and 6*c* show caspase activity measured in 293 cell extracts in the presence of His$_6$-HBX or control [CTR] proteins, purified His$_6$-HBXIP, purified Survivin, or various combinations of these proteins after Cytochrome c and dATP were added. FIG. 6*d* shows the results of immunoprecipitation using anti-Survivin antibody (upper panel) of lysates of HEK 293 cell expressing FLAG-tagged-HBX or FLAG-SIP (as a control) together with Myc-Survivin or HA-HBXIP with anti-FLAG epitope antibody demonstrates increased association of Survivin with HBX when HBXIP was co-expressed (compare last two lanes at right). FIG. 6*e* shows the results when His$_6$-pro-Caspase-9 was incubated with GST-HBXIP (+) or GST-CD40 control protein (−), in the presence or absence of His$_6$-HBX and untagged Survivin. GST-fusion proteins were recovered on glutathione-Sepharose and bound proteins were detected by immunoblotting using anti-Caspase-9, anti-Survivin, or anti-HBX antisera. FIG. 6*f* shows immunoblotting using anti-Survivin antibody (top panel) of HepG2 cell extracts immunodepleted using anti-Survivin antisera or preimmune serum (CTR). Then extracts were analyzed for Caspase activity based on Ac-DEVD-AFC cleavage, where lysates were incubated with recombinant HBX (+) or control protein (−) prior to stimulation with Cytochrome c and dATP.

DETAILED DESCRIPTION OF THE PREFERRED EMBODIMENT

Figure 1:
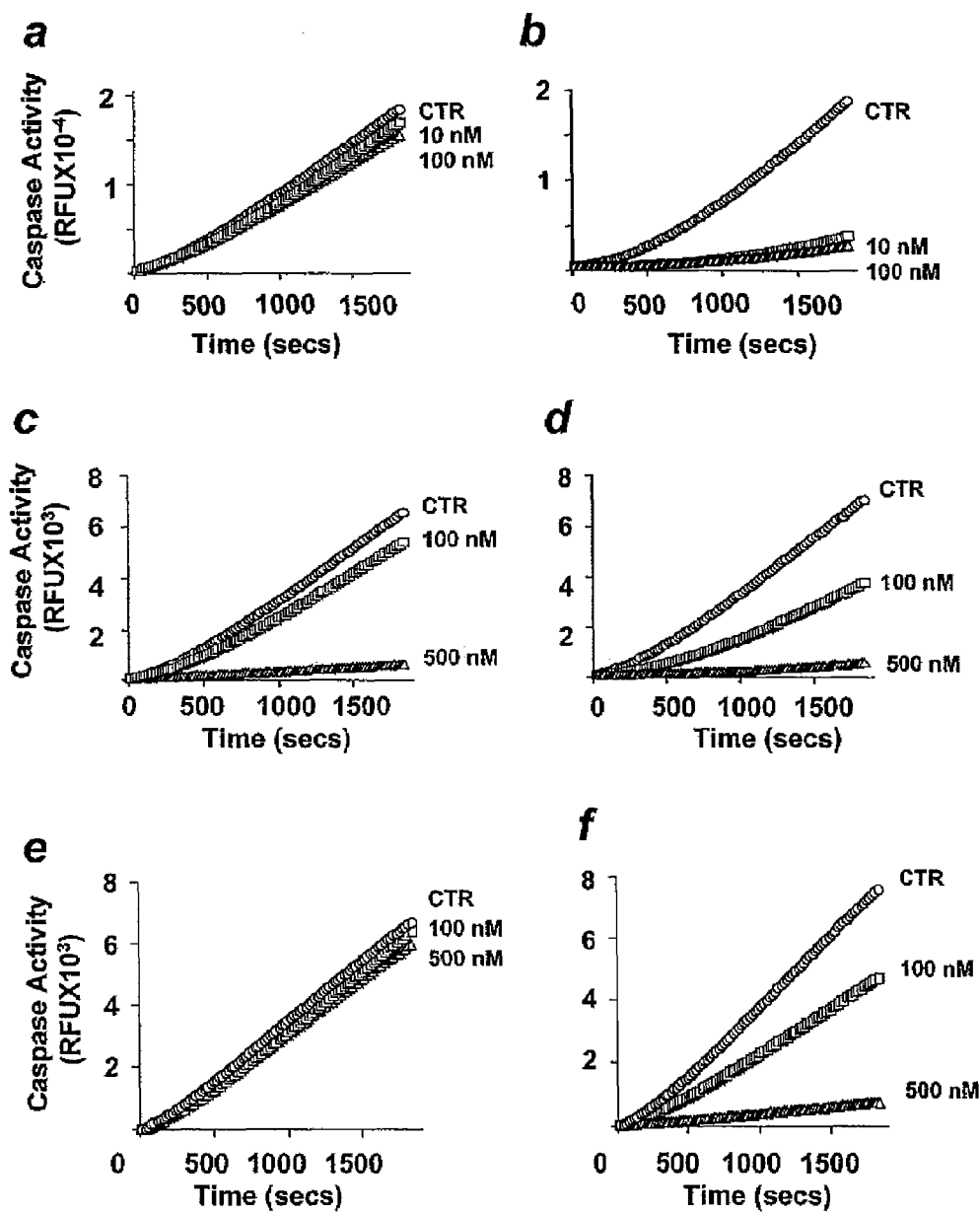
FIG. 1(*a-f*) shows differences in Caspase suppression by Survivin and XIAP. Effects of purified Survivin (FIGS. 1*a*, 1*c*, 1*e*) and XIAP (FIGS. 1*b*, 1*d*, 1*f*) on recombinant active Caspase-3 (FIGS. 1*a*, 1*b*) or on caspase-3-like protease activity induced in cell extracts by Cytochrome c (FIGS. 1*c*, 1*d*, 1*e*, 1*f*) are shown.

Survivin is an anti-apoptotic protein of undefined mechanism, which is pathologically over-expressed in most human cancers. It has been discovered that Survivin forms complexes with an endogenous cellular protein, Hepatitis B X-interacting protein (HBXIP), which was originally recognized for its association with the X protein of Hepatitis B Virus (HBX). Survivin/HBXIP complexes, but neither Survivin nor HBXIP individually, bind pro-Caspase-9, preventing its recruitment to Apaf1, and thereby selectively suppress apoptosis initiated via the mitochondria/Cytochrome C pathway. Viral HBX protein also interacts with the Survivin/HBXIP complex and suppresses Caspase activation in a Survivin-dependent manner. Thus, HBXIP functions as a cofactor for Survivin, and serves as a link between the cellular apoptosis machinery and a viral pathogen involved on an epidemic scale in hepatocellular carcinogenesis.

In an effort to provide insights into the anti-apoptotic mechanism of Survivin, cDNA libraries were screened for Survivin-binding proteins, resulting in the discovery that hepatitis B X-interacting protein (HBXIP) associates with p17 Survivin. HBXIP was originally identified by virtue of its ability to interact with the HBX protein of Hepatitis B Virus (HBV) (Melegari, M. et al. 1998 *J Virol* 72:1737-1743). HBX is a putative oncogenic protein, which has been previously implicated in regulation of apoptosis, as well as other processes (reviewed in Murakami, S. 2001 *J Gastroenterol* 36:651-660). HBXIP operates as a cofactor for Survivin, allowing it to bind and suppress activation of pro-Caspase-9, the apical protease in a mitochondrial pathway for cell death. These findings thus provide novel insights into the anti-apoptotic mechanism of Survivin, and provide a link between Survivin and neoplastic diseases associated with HBV infection.

Some embodiments of the present invention relate to methods of inhibiting the interaction between Survivin and HBXIP both in vitro and in vivo thereby resulting in the enhancement of apoptosis. Methods of inhibiting such interactions include, but are not limited to, reducing the level or expression of the Survivin and/or HBXIP protein by inhibiting transcription, stability or processing of the Survivin and/or HBXIP mRNA; inhibiting or altering post-translation processing of the Survivin and/or HBXIP protein; or interfering with the interaction between Survivin and HBXIP.

A number of different methods of inhibiting the interaction between Survivin and HBXIP are disclosed herein. For example, nucleic acids or nucleic acid-like compounds can be used to reduce the expression of the Survivin and/or HBXIP gene. Such nucleic acids and nucleic acid-like compounds can include DNA, RNA, peptide nucleic acid (PNA), or modified polynucleotides. Such nucleic acids can function as antisense nucleic acids, catalytic RNAs (ribozymes), and small interfering RNAs (siRNAs), such as dsRNAs. In other embodiments, antibodies can be prepared which have affinity for and bind to either Survivin or HBXIP. Such antibodies can be used to prevent disrupt or otherwise inhibit the interaction between Survivin and HBXIP. Molecular decoys can also be used to prevent, disrupt or otherwise inhibit the interaction between Survivin and HBXIP. In some embodiments, the molecular decoys are peptides or peptidomimetics which comprise the portion of the Survivin or HBXIP polypeptide which facilitates interaction between Survivin and HBXIP but lacks a sufficient homology with the full-length Survivin or HBXIP polypeptide to permit formation of a complex that inhibits apoptosis. In such embodiments, the peptides or peptidomimetics act as competitive inhibitors of the interaction between Survivin and HBXIP. In addition to the above embodiments, small molecules can be used to inhibit the interaction between Survivin and HBXIP. Such molecules can be obtained, for example, by screening synthetic or natural product libraries.

Other embodiments of the present invention relate to methods of enhancing the interaction between Survivin and HBXIP both in vitro and in vivo thereby resulting in the inhibition of apoptosis. Methods of enhancing such interactions include, but are not limited to, increasing the level or expression of the Survivin and/or HBXIP protein by enhancing transcription and/or stability of the Survivin and/or HBXIP mRNA or facilitating the interaction between Survivin and HBXIP.

A number of different methods of enhancing the interaction between Survivin and HBXIP are disclosed herein. For example, antibodies can be prepared which have affinity for, and thus bind to, an epitope that is created upon the formation of the complex that results from the binding of Survivin and HBXIP. Such antibodies can be used to facilitate complex formation between Survivin and HBXIP. In addition to the above embodiments, small molecules can be used to facilitate the interaction between Survivin and HBXIP. Such molecules can be obtained, for example, by screening synthetic or natural product libraries. Additionally, methods of increasing the production of a protein by increasing its transcription and/or translation efficiency can be used to increase the amount of one or both of Survivin and HBXIP thereby increasing the amount of protein available for complex formation.

In some embodiments of the present invention, the cells in which apoptosis is inhibited or enhanced include, but are not limited to, human cells as well as those of other vertebrate animals including fish, avian, cattle, goat, pig, sheep, rodent, hamster, mouse, rat, and primate. Cells which are targeted can also be from the germ line or somatic, totipotent or pluripotent, dividing or non-dividing, parenchyma or epithelium, immortalized or transformed, or the like. The cell may be a stem cell or a differentiated cell. Cell types that are differentiated include adipocytes, fibroblasts, myocytes, cardiomyocytes, endothelium, neurons, glia, blood cells, megakaryocytes, lymphocytes, macrophages, neutrophils, eosinophils, basophils, mast cells, leukocytes, granulocytes, keratinocytes, chondrocytes, osteoblasts, osteoclasts, hepatocytes, and cells of the endocrine or exocrine glands. In some embodiments of the present invention, the cells are neoplastic cells within humans and/or other animals.

Antisense Nucleic Acids

Antisense nucleic acids that are used to reduce the amount of Survivin and/or HBXIP polypeptides that is present inside a cell are complementary to at least a portion of the coding strand of either Survivin (SEQ ID NO: 1) or HBXIP (SEQ ID NO: 3). Such antisense nucleic acids include antisense polynucleotides complementary to the full-length sense strand of Survivin and/or HBXIP or oligonucleotide fragments from at least about 15 to more than about 120 nucleotides, including at least about 16 nucleotides, at least about 17 nucleotides, at least about 18 nucleotides, at least about 19 nucleotides, at least about 20 nucleotides, at least about 21 nucleotides, at least about 22 nucleotides, at least about 23 nucleotides, at least about 24 nucleotides, at least about 25 nucleotides, at least about 26 nucleotides, at least about 27 nucleotides, at least about 28 nucleotides, at least about 29 nucleotides, at least about 30 nucleotides, at least about 35 nucleotides, at least about 40 nucleotides, at least about 45 nucleotides, at least about 50 nucleotides, at least about 55 nucleotides, at least about 60 nucleotides, at least about 65 nucleotides, at least about 70 nucleotides, at least about 75 nucleotides, at least about 80 nucleotides, at least about 85 nucleotides, at least about 90 nucleotides, at least about 95 nucleotides, at least about 100 nucleotides, at least about 110 nucleotides, at least about 120 nucleotides or greater than 120 nucleotides.

As used herein, the term "oligonucleotide" refers to an oligomer or polymer of ribonucleic acid (RNA) or deoxyribonucleic acid (DNA) or mimetics thereof. This term includes oligonucleotides composed of naturally-occurring nucleobases, sugars and covalent internucleoside (backbone) linkages as well as oligonucleotides having non-naturally-occurring portions which function similarly. Such modified or substituted oligonucleotides are often preferred over native forms because of desirable properties such as, for example, enhanced cellular uptake, enhanced affinity for nucleic acid target and increased stability in the presence of nucleases.

While antisense oligonucleotides are a preferred form of antisense compound, embodiments of the present invention contemplates other oligomeric antisense compounds, including but not limited to, oligonucleotide mimetics such as are described below. The antisense oligonucleotides described herein also include ribozymes, external guide sequence (EGS) oligonucleotides (oligozymes), and other short catalytic RNAs or catalytic oligonucleotides which hybridize to the target nucleic acid and modulate its expression.

As is known in the art, a nucleoside is a base-sugar combination. The base portion of the nucleoside is normally a heterocyclic base. The two most common classes of such heterocyclic bases are the purines and the pyrimidines. Nucleotides are nucleosides that further include a phosphate group covalently linked to the sugar portion of the nucleoside. For those nucleosides that include a pentofuranosyl sugar, the phosphate group can be linked to either the 2', 3' or 5' hydroxyl moiety of the sugar. In forming oligonucleotides, the phosphate groups covalently link adjacent nucleosides to one another to form a linear polymeric compound. In turn the respective ends of this linear polymeric structure can be further joined to form a circular structure, however, open linear structures are generally preferred. Within the oligonucleotide structure, the phosphate groups are commonly referred to as forming the internucleoside backbone of the oligonucleotide. The normal linkage or backbone of RNA and DNA is a 3' to 5' phosphodiester linkage.

Specific examples of antisense compounds useful in certain embodiments of this invention include oligonucleotides containing modified backbones or non-natural internucleoside linkages. As used herein, oligonucleotides having modified backbones include those that retain a phosphorus atom in the backbone and those that do not have a phosphorus atom in the backbone. For the purposes of this specification, and as sometimes referenced in the art, modified oligonucleotides that do not have a phosphorus atom in their internucleoside backbone can also be considered to be oligonucleosides.

In some embodiments modified oligonucleotide backbones include, for example, phosphorothioates, chiral phosphorothioates, phosphorodithioates, phosphotriesters, aminoalkylphosphotriesters, methyl and other alkyl phosphonates including 3'-alkylene phosphonates, 5'-alkylene phosphonates and chiral phosphonates, phosphinates, phosphoramidates including 3'-amino phosphoramidate and aminoalkylphosphoramidates, thionophosphoramidates, thionoalkylphosphonates, thionoalkylphosphotriesters, selenophosphates and borano-phosphates having normal 3'-5' linkages, 2'-5' linked analogs of these, and those having inverted polarity wherein one or more internucleotide linkages is a 3' to 3', 5' to 5' or 2' to 2' linkage. Certain oligonucleotides having inverted polarity comprise a single 3' to 3' linkage at the 3'-most internucleotide linkage i.e. a single inverted nucleoside residue which may be abasic (the nucleobase is missing or has a hydroxyl group in place thereof). Various salts, mixed salts and free acid forms are also included.

In some embodiments modified oligonucleotide backbones that do not include a phosphorus atom therein have backbones that are formed by short chain alkyl or cycloalkyl internucleoside linkages, mixed heteroatom and alkyl or cycloalkyl internucleoside linkages, or one or more short chain heteroatomic or heterocyclic internucleoside linkages. These include those having morpholino linkages (formed in part from the sugar portion of a nucleoside); siloxane backbones; sulfide, sulfoxide and sulfone backbones; formacetyl and thioformacetyl backbones; methylene formacetyl and thioformacetyl backbones; riboacetyl backbones; alkene containing backbones; sulfamate backbones; methyleneimino and methylenehydrazino backbones; sulfonate and sulfonamide backbones; amide backbones; and others having mixed N, O, S and $CH_2$ component parts.

In other embodiments, oligonucleotide mimetics, both the sugar and the internucleoside linkage, i.e., the backbone, of the nucleotide units are replaced with novel groups. The base units are maintained for hybridization with an appropriate nucleic acid target compound. One such oligomeric compound, an oligonucleotide mimetic that has been shown to have excellent hybridization properties, is referred to as a peptide nucleic acid (PNA). In PNA compounds, the sugar-backbone of an oligonucleotide is replaced with an amide containing backbone, in particular an aminoethylglycine backbone. The nucleobases are retained and are bound directly or indirectly to aza nitrogen atoms of the amide portion of the backbone. Representative United States patents that teach the preparation of PNA compounds include, but are not limited to, U.S. Pat. Nos. 5,539,082; 5,714,331; and 5,719,262, each of which is herein incorporated by reference. Further teaching of PNA compounds can be found in Nielsen et al., Science, 1991, 254, 1497-1500.

In still other embodiments of the present invention, the expression of Survivin and/or HBXIP is modulated using oligonucleotides with phosphorothioate backbones and oligonucleosides with heteroatom backbones. Modified oligonucleotides may also contain one or more substituted sugar moieties. In some embodiments oligonucleotides comprise one of the following at the 2' position: OH; F; O-, S-, or N-alkyl; O-, S-, or N-alkenyl; O-, S- or N-alkynyl; or O-alkyl-O-alkyl, wherein the alkyl, alkenyl and alkynyl may be substituted or unsubstituted $C_1$ to $C_{10}$ alkyl or $C_2$ to $C_{10}$ alkenyl and alkynyl. Particularly preferred are $O[(CH_2)_nO]_mCH_3$, $O(CH_2)_nOCH_3$, $O(CH_2)_nNH_2$, $O(CH_2)_nCH_3$, $O(CH_2)_nONH_2$ and $O(CH_2)_nON[(CH_2)_nCH_3)]_2$, where n and m are from 1 to about 10. Other preferred oligonucleotides comprise one of the following at the 2' position: $C_1$ to $C_{10}$ lower alkyl, substituted lower alkyl, alkenyl, alkynyl, alkaryl, aralkyl, O-alkaryl or O-aralkyl, SH, $SCH_3$, OCN, Cl, Br, CN, $CF_3$, $OCF_3$, $SOCH_3$, $SO_2CH_3$, $ONO_2$, $NO_2$, $N_3$, $NH_2$, heterocycloalkyl, heterocycloalkaryl, aminoalkylamino, polyalkylamino, substituted silyl, an RNA cleaving group, a reporter group, an intercalator, a group for improving the pharmacokinetic properties of an oligonucleotide, or a group for improving the pharmacodynamic properties of an oligonucleotide, and other substituents having similar properties. Another modification includes 2'-methoxyethoxy (2'OCH$_2$CH$_2$OCH$_3$, also known as 2'-O-(2-methoxyethyl) or 2'-MOE) (Martin et al., Helv. Chim. Acta, 1995, 78, 486-504).

An embodiment of the present invention includes the use of Locked Nucleic Acids (LNAs) to generate antisense nucleic acids having enhanced affinity and specificity for the target polynucleotide. LNAs are nucleic acid in which the 2'-hydroxyl group is linked to the 3' or 4' carbon atom of the sugar ring thereby forming a bicyclic sugar moiety. The linkage is preferably a methelyne (—CH$_2$—)n group bridging the 2' oxygen atom and the 4' carbon atom wherein n is 1 or 2. LNAs and preparation thereof are described in WO 98/39352 and WO 99/14226.

Other modifications include 2'-methoxy(2'-O—CH$_3$), 2'-aminopropoxy(2'-OCH$_2$CH$_2$CH$_2$NH$_2$), 2'-allyl (2'-CH=CH=CH$_2$), 2'-O-allyl (2'-O—CH$_2$—CH=CH$_2$) and 2'-fluoro (2'-F). The 2'-modification may be in the arabino (up) position or ribo (down) position. A preferred 2'-arabino modification is 2'-F. Similar modifications may also be made at other positions on the oligonucleotide, particularly the 3' position of the sugar on the 3' terminal nucleotide or in 2'-5' linked oligonucleotides and the 5' position of 5' terminal nucleotide. Oligonucleotides may also have sugar mimetics such as cyclobutyl moieties in place of the pentofuranosyl sugar.

Oligonucleotides may also include nucleobase (often referred to in the art simply as "base") modifications or substitutions. As used herein, "unmodified" or "natural" nucleobases include the purine bases adenine (A) and guanine (G), and the pyrimidine bases thymine (T), cytosine (C) and uracil (U). Modified nucleobases include other synthetic and natural nucleobases such as 5-methylcytosine, 5-hydroxymethyl cytosine, xanthine, hypoxanthine, 2-aminoadenine, 6-methyl and other alkyl derivatives of adenine and guanine, 2-propyl and other alkyl derivatives of adenine and guanine, 2-thiouracil, 2-thiothymine and 2-thiocytosine, 5-halouracil and cytosine, 5-propynyl uracil and cytosine and other alkynyl derivatives of pyrimidine bases, 6-azo uracil, cytosine and thymine, 5-uracil (pseudouracil), 4-thiouracil, 8-halo, 8-amino, 8-thiol, 8-thioalkyl, 8-hydroxyl and other 8-substituted adenines and guanines, 5-halo particularly 5-bromo, 5-trifluoromethyl and other 5-substituted uracils and cytosines, 7-methylguanine and 7-methyladenine, 2-F-adenine, 2-amino-adenine, 8-azaguanine and 8-azaadenine, 7-deazaguanine and 7-deazaadenine and 3-deazaguanine and 3-deazaadenine. Further modified nucleobases include tricyclic pyrimidines such as phenoxazine cytidine (1H-pyrimido[5,4-b][1,4]benzoxazi-n-2(3H)-one), phenothiazine cytidine (1H-pyrimido[5,4-b][1,4]benzothiazin-2(3H)-one), G-clamps such as a substituted phenoxazine cytidine (e.g. 9-(2-aminoethoxy)-H-pyrimido[5,4-b][1,4]benzoxazin-2 (3H)-one), carbazole cytidine (2H-pyrimido[4,5-b]indol-2-one), pyridoindole cytidine (H-pyrimido[3',2':4,5]pyrrolo[2,3-d]pyrimidin-2-one). Modified nucleobases may also include those in which the purine or pyrimidine base is replaced with other heterocycles, for example 7-deaza-adenine, 7-deazaguanosine, 2-aminopyridine and 2-pyridone. Further nucleobases include those disclosed in U.S. Pat. No. 3,687,808, those disclosed in The Concise Encyclopedia Of Polymer Science And Engineering, pages 858-859, Kroschwitz, J. I., ed. John Wiley & Sons, 1990, those disclosed by Englisch et al., Angewandte Chemie, International Edition, 1991, 30, 613, and those disclosed by Sanghvi, Y. S., Chapter 15, Antisense Research and Applications, pages 289-302, Crooke, S. T. and Lebleu, B. ed., CRC Press, 1993. Certain of these nucleobases are particularly useful for increasing the binding affinity of the oligomeric compounds described herein. These include 5-substituted pyrimidines, 6-azapyrimidines and N-2, N-6 and O-6 substituted purines, including 2-aminopropyladenine, 5-propynyluracil and 5-propynylcytosine. 5-methylcytosine substitutions have been shown to increase nucleic acid duplex stability by 0.6-1.2° C. (Sanghvi, Y. S., Crooke, S. T. and Lebleu, B., eds., Antisense Research and Applications, CRC Press, Boca Raton, 1993, pp. 276-278) and are presently preferred base substitutions, even more particularly when combined with 2'-O-methoxyethyl sugar modifications.

Another modification of the antisense oligonucleotides described herein involves chemically linking to the oligonucleotide one or more moieties or conjugates which enhance the activity, cellular distribution or cellular uptake of the oligonucleotide. The antisense oligonucleotides can include conjugate groups covalently bound to functional groups such as primary or secondary hydroxyl groups. Conjugate groups include intercalators, reporter molecules, polyamines, polyamides, polyethylene glycols, polyethers, groups that enhance the pharmacodynamic properties of oligomers, and groups that enhance the pharmacokinetic properties of oligomers. Typical conjugates groups include cholesterols, lipids, phospholipids, biotin, phenazine, folate, phenanthridine, anthraquinone, acridine, fluoresceins, rhodamines, coumarins, and dyes. Groups that enhance the pharmacodynamic properties, in the context of this invention, include groups that improve oligomer uptake, enhance oligomer resistance to degradation, and/or strengthen sequence-specific hybridization with RNA. Groups that enhance the pharmacokinetic properties, in the context of this invention, include groups that improve oligomer uptake, distribution, metabolism or excretion. Conjugate moieties include but are not limited to lipid moieties such as a cholesterol moiety (Letsinger et al., Proc. Natl. Acad. Sci. USA, 1989, 86, 6553-6556), cholic acid (Manoharan et al., Bioorg. Med. Chem. Let., 1994, 4, 1053-1060), a thioether, e.g., hexyl-5-tritylthiol (Manoharan et al., Ann. N.Y. Acad. Sci., 1992, 660, 306-309; Manoharan et al., Bioorg. Med. Chem. Let., 1993, 3, 2765-2770), a thiocholesterol (Oberhauser et al., Nucl. Acids Res., 1992, 20, 533-538), an aliphatic chain, e.g., dodecandiol or undecyl residues (Saison-Behmoaras et al., EMBO J., 1991, 10, 1111-1118; Kabanov et al., FEBS Lett., 1990, 259, 327-330; Svinarchuk et al., Biochimie, 1993, 75, 49-54), a phospholipid, e.g., dihexadecyl-rac-glycerol or triethylammonium 1,2-di-O-hexadecyl-rac-glycero-3-H-phosphonate (Manoharan et al., Tetrahedron Lett., 1995, 36, 3651-3654; Shea et al., Nucl. Acids Res., 1990, 18, 3777-3783), a polyamine or a polyethylene glycol chain (Manoharan et al., Nucleosides & Nucleotides, 1995, 14, 969-973), or adamantane acetic acid (Manoharan et al., Tetrahedron Lett., 1995, 36, 3651-3654), a palmityl moiety (Mishra et al., Biochim. Biophys. Acta, 1995, 1264, 229-237), or an octadecylamine or hexylaminocarbonyloxycholesterol moiety (Crooke et al., J. Pharmacol. Exp. Ther., 1996, 277, 923-937.

It is not necessary for all positions in a given compound to be uniformly modified, and in fact more than one of the aforementioned modifications may be incorporated in a single compound or even at a single nucleoside within an oligonucleotide. The methods described herein also contemplate the use of antisense compounds which are chimeric compounds. "Chimeric" antisense compounds or "chimeras," as used herein, are antisense compounds, particularly oligonucleotides, which contain two or more chemically distinct regions, each made up of at least one monomer unit, i.e., a nucleotide in the case of an oligonucleotide compound. These oligonucleotides typically contain at least one region wherein the oligonucleotide is modified so as to confer upon the oligonucleotide increased resistance to nuclease degradation, increased cellular uptake, and/or increased binding affinity for the target nucleic acid. An additional region of the oligonucleotide may serve as a substrate for enzymes capable of cleaving RNA:DNA or RNA:RNA hybrids. By way of example, RNase H is a cellular endonuclease which cleaves the RNA strand of an RNA:DNA duplex. Activation of RNase H, therefore, results in cleavage of the RNA target, thereby greatly enhancing the efficiency of oligonucleotide inhibition of gene expression. Consequently, comparable results can often be obtained with shorter oligonucleotides when chimeric oligonucleotides are used, compared to phosphorothioate deoxyoligonucleotides hybridizing to the same target region. Cleavage of the RNA target can be routinely detected by gel electrophoresis and, if necessary, associated nucleic acid hybridization techniques known in the art.

Chimeric antisense compounds for use in the methods of the present invention may be formed as composite structures of two or more oligonucleotides, modified oligonucleotides, oligonucleosides and/or oligonucleotide mimetics as described above. Such compounds have also been referred to in the art as hybrids or gapmers.

The antisense compounds used in accordance with some embodiments of this invention may be conveniently and routinely made through the well-known technique of solid phase synthesis. Equipment for such synthesis is sold by several vendors including, for example, Applied Biosystems (Foster City, Calif.). Any other means for such synthesis known in the art may additionally or alternatively be employed. It is well known to use similar techniques to prepare oligonucleotides such as the phosphorothioates and alkylated derivatives.

The antisense compounds for use with the methods described herein encompass any pharmaceutically acceptable salts, esters, or salts of such esters, or any other compound which, upon administration to an animal including a human, is capable of providing (directly or indirectly) the biologically active metabolite or residue thereof.

In some embodiments of the present invention, an antisense nucleic acid specific to the Survivin and/or the HBXIP gene is synthesized and introduced directly into a subject. In other embodiments, the antisense nucleic acid can be formulated as part of a targeted delivery system, such as a target specific liposome, which specifically recognizes and delivers the antisense nucleic acid to an appropriate tissue or cell type, such as a tumor cell. Upon administration of the targeted antisense nucleic acid to a subject, the antisense nucleic acid is delivered to the appropriate cell type thereby increasing the concentration antisense nucleic acid within the cell type.

In other embodiments of the present invention, an appropriate cell or tissue is provided with expression construct which comprises a nucleic acid that encodes the antisense RNA that is specific to the Survivin and/or the HBXIP gene. In these embodiments, the nucleic acid that encoding the antisense RNA can be placed under the control of either a constitutive or a regulatable promoter.

Interfering RNA

Some embodiments of the present invention provide a method of producing sequence-specific inhibition of the expression of either the Survivin and/or the HBXIP gene by introducing a small inhibitory RNA (siRNA). As used herein siRNAs are synonymous with double-stranded RNA (dsRNA), and include double-stranded RNA oligomers with or without hairpin structures at each end. Small interfering RNAs comprise oligonucleotides of at least about 15 to greater than about 120 nucleotides, including at least about 16 nucleotides, at least about 17 nucleotides, at least about 18 nucleotides, at least about 19 nucleotides, at least about 20 nucleotides, at least about 21 nucleotides, at least about 22 nucleotides, at least about 23 nucleotides, at least about 24 nucleotides, at least about 25 nucleotides, at least about 26 nucleotides, at least about 27 nucleotides, at least about 28 nucleotides, at least about 29 nucleotides, at least about 30 nucleotides, at least about 35 nucleotides, at least about 40 nucleotides, at least about 45 nucleotides, at least about 50 nucleotides, at least about 55 nucleotides, at least about 60 nucleotides, at least about 65 nucleotides, at least about 70 nucleotides, at least about 75 nucleotides, at least about 80 nucleotides, at least about 85 nucleotides, at least about 90 nucleotides, at least about 95 nucleotides, at least about 100 nucleotides, at least about 110 nucleotides, at least about 120 nucleotides or greater than 120 nucleotides. In certain embodiments of the present invention, the siRNA comprises an oligonucleotide from about 21 to about 25 nucleotides in length. In some embodiments, the siRNA molecule is a heteroduplex of RNA and DNA.

As with antisense nucleic acids, siRNAs can include modifications to either the phosphate-sugar backbone or the nucleoside. For example, the phosphodiester linkages of natural RNA may be modified to include at least one of a nitrogen or sulfur heteroatom. Modifications in RNA structure may be tailored as described for antisense nucleic acids.

A process for inhibiting expression of the Survivin and/or the HBXIP gene in a cell comprises introduction of an siRNA with partial or fully double-stranded character into the cell. Inhibition is sequence-specific in that a nucleotide sequence from a portion of the Survivin and/or the HBXIP gene is chosen to produce inhibitory RNA. Depending on the dose of siRNA delivered, this process can provide partial or complete loss of function for the Survivin and/or the HBXIP gene.

In some embodiments of the present invention, an siRNA specific to the Survivin and/or the HBXIP gene is synthesized and introduced directly into a subject. In other embodiments, the siRNA can be formulated as part of a targeted delivery system, such as a target specific liposome, which specifically recognizes and delivers the siRNA to an appropriate tissue or cell type, such as a tumor cell. Upon administration of the targeted siRNA to a subject, the siRNA is delivered to the appropriate cell type, thereby increasing the concentration siRNA within the cell type.

In other embodiments of the present invention, an appropriate cell or tissue is provided with expression construct which comprises a nucleic acid that encodes one or both strands of an siRNA that is specific to the Survivin and/or the HBXIP gene. In these embodiments, the nucleic acid that encodes one or both strands of the siRNA can be placed under the control of either a constitutive or a regulatable promoter. In some embodiments, the nucleic acid encodes an siRNA that forms a hairpin structure.

Inhibition of Gene Expression Using Nucleic Acids

Inhibition of gene expression refers to the absence (or observable decrease) in the level of protein and/or mRNA product from the Survivin and/or the HBXIP gene. The consequences of inhibition can be confirmed by examination of the outward properties of the cell or organism, such as increased apoptosis, or by biochemical techniques, such as determining the amount of Caspase-9 activity or directly measuring levels of the Survivin and/or the HBXIP transcript. For a cell line or whole organism, gene expression is conveniently assayed by use of a reporter or drug resistance gene whose protein product is easily assayed. Such reporter genes include acetohydroxyacid synthase (AHAS), alkaline phosphatase (AP), beta galactosidase (LacZ), beta glucoronidase (GUS), chloramphenicol acetyltransferase (CAT), green fluorescent protein (GFP), horseradish peroxidase (HRP), luciferase (Luc), nopaline synthase (NOS), octopine synthase (OCS), and derivatives thereof. Multiple selectable markers are available that confer resistance to ampicillin, bleomycin, chloramphenicol, gentamycin, hygromycin, kanamycin, lincomycin, methotrexate, phosphinothricin, puromycin, and tetracyclin.

Depending on the assay, quantitation of the amount of gene expression allows one to determine a degree of inhibition which is greater than 10%, 33%, 50%, 90%, 95% or 99% as compared to an untreated cell. Lower doses of injected material and longer times after administration of the antisense nucleic acid, catalytic RNA or siRNA may result in inhibition in partial inhibition of the Survivin and/or HBXIP genes.

Antisense nucleic acids, catalytic RNAs and siRNAs comprising a nucleotide sequences identical to a portion of the Survivin and/or HBXIP genes are contemplated in some embodiments of the present invention. However, nucleic acid sequences with insertions, deletions, and single point mutations relative to the target sequence are also effective for inhibition of gene expression. Thus, sequence identity may optimized by sequence comparison and alignment algorithms known in the art (see Gribskov and Devereux, Sequence Analysis Primer, Stockton Press, 1991, and references cited therein) and calculating the percent difference between the nucleotide sequences by, for example, the Smith-Waterman algorithm as implemented in the BESTFIT software program using default parameters (e.g., University of Wisconsin Genetic Computing Group). Greater than 90% sequence identity, or even 100% sequence identity, between the siRNA and the portion of the target gene is preferred. Alternatively, the duplex region of the RNA may be defined functionally as a nucleotide sequence that is capable of hybridizing with a portion of the target gene transcript. Exemplary hybridization conditions are 400 mM NaCl, 40 mM PIPES pH 6.4, 1 mM EDTA, 50° C. or 70° C. hybridization for 12-16 hours; followed by washing.

Antibodies

Some embodiments of the present invention related to the use of antibodies that bind to an epitope present on the Survivin polypeptide (SEQ ID NO: 2) or the HBXIP polypeptide (SEQ ID NO: 4) to interfere with the interaction between Survivin and HBXIP thereby resulting in an enhancement of apoptosis. Other embodiments of the present invention relate to the use of antibodies which recognize an epitope that is specific to the formed Survivin/HBXIP complex thereby enhancing the interaction between Survivin and HBXIP. Enhancement of Survivin/HBXIP interaction results in an inhibition of apoptosis.

Antibodies and fragments can be made by standard methods (See, for example, E. Harlow et al., Antibodies, A Laboratory Manual, Cold Spring Harbor Laboratory, Cold Spring Harbor, N.Y., 1988). However, the isolation, identification, and molecular construction of antibodies has been developed to such an extent that the choices are almost inexhaustible. Therefore, examples of antibody parts, and complexes will be provided with the understanding that this can only represent a sampling of what is available.

In one embodiment of the present invention, the antibody is a single chain Fv region. Antibody molecules have two generally recognized regions, in each of the heavy and light chains. These regions are the so-called "variable" region which is responsible for binding to the specific antigen in question, and the so-called "constant" region which is responsible for biological effector responses such as complement binding, binding to neutrophils and macrophages, etc. The constant regions are not necessary for antigen binding. Accordingly, constant regions can be separated from the antibody molecule leaving only the variable binding regions.

The variable regions of an antibody are composed of a light chain and a heavy chain. Light and heavy chain variable regions have been cloned and expressed in foreign hosts, while maintaining their binding ability. Therefore, it is possible to generate a single chain structure from the multiple chain aggregate (the antibody), such that the single chain structure will retain the three-dimensional architecture of the multiple chain aggregate.

Fv fragments which are single polypeptide chain binding proteins having the characteristic binding ability of multi-chain variable regions of antibody molecules, can be used in the methods described herein. These fragments are produced, for example, following the methods of Ladner et al., U.S. Pat. No. 5,260,203, issued Nov. 9, 1993, using a computer based system and method to determine chemical structures. These chemical structures are used for converting two naturally aggregated but chemically separated light and heavy polypeptide chains from an antibody variable region into a single polypeptide chain which will fold into a three dimensional structure very similar to the original structure of the two polypeptide chains. The two regions may be linked using an amino acid sequence as a bridge.

The single polypeptide chain obtained from this method can then be used to prepare a genetic sequence coding therefor. The genetic sequence can then be replicated in appropriate hosts, further linked to control regions, and transformed into expression hosts, wherein it can be expressed. The resulting single polypeptide chain binding protein, upon refolding, has the binding characteristics of the aggregate of the original two (heavy and light) polypeptide chains of the variable region of the antibody.

In a further embodiment, the antibodies are multivalent forms of single-chain antigen-binding proteins. Multivalent forms of single-chain antigen-binding proteins have significant utility beyond that of the monovalent single-chain antigen-binding proteins. A multivalent antigen-binding protein has more than one antigen-binding site which results in an enhanced binding affinity. The multivalent antibodies can be produced using the method disclosed in Whitlow et al., U.S. Pat. No. 5,869,620, issued Feb. 9, 1999. The method involves producing a multivalent antigen-binding protein by linking at least two single-chain molecules, each single chain molecule having two binding portions of the variable region of an antibody heavy or light chain linked into a single chain protein. In this way the antibodies can have binding sites for different parts of an antigen or have binding sites for multiple antigens.

In one embodiment, the antibody is an oligomer. The oligomer is produced as in PCT/EP97/05897, filed Oct. 24, 1997, by first isolating a specific ligand from a phage-displayed library. Oligomers overcome the problem of the isolation of mostly low affinity ligands from these libraries, by oligomerizing the low-affinity ligands to produce high affinity oligomers. The oligomers are constructed by producing a fusion protein with the ligand fused to a semi-rigid hinge and a coiled coil domain from Cartilage Oligomeric Matrix Protein (COMP). When the fusion protein is expressed in a host cell, it self assembles into oligomers.

In some embodiments, the oligomers are peptabodies (Terskikh et al., Biochemistry 94:1663-1668 (1997)). Peptabodies can be exemplified as IgM antibodies which are pentameric with each binding site having low-affinity binding, but able to bind in a high affinity manner as a complex. Peptabodies are made using phage-displayed random peptide libraries. A short peptide ligand from the library is fused via a semi-rigid hinge at the N-terminus of the COMP (cartilage oligomeric matrix protein) pentamerization domain. The fusion protein is expressed in bacteria where it assembles into a pentameric antibody which shows high affinity for its target. Depending on the affinity of the ligand, an antibody with very high affinity can be produced.

In some embodiments the antibody, antibody part or antibody complex is derived from humans or is "humanized" (i.e. non-immunogenic in a human) by recombinant or other technology. Such antibodies are the equivalents of the monoclonal and polygonal antibodies disclosed herein, but are less immunogenic, and are better tolerated by the patient.

Humanized antibodies may be produced, for example, by replacing an immunogenic portion of an antibody with a corresponding, but non-immunogenic portion (i.e. chimeric antibodies) (See, for example, Robinson, et al., PCT Application No. PCT/US86/02269; Akira, et al., European Patent Application No. 184,187; Taniguchi, European Patent Application No. 171,496; Morrison, et al., European Patent Application No. 173,494; Neuberger, et al., International Patent Publication No. WO86/01533; Cabilly, et al., European Patent Application No. 125,023; Better, et al., *Science* 240: 1041-1043 (1988); Liun, et al., *Proc. Natl. Acad. Sci. USA* 84:3439-3433 (1987); Liu, et al., *J. Immunol.* 139:3521-3526 (1987); Sun, et al., *Proc. Natl. Acad. Sci. USA* 84:214-218 (1987); Nishimura, et al., *Canc. Res.* 47:999-1005 (1987); Wood, et al., *Nature* 314:446-449 (1985)); Shaw et al., *J. Natl. Cancer Inst.* 80:1553-1559 (1988); all of which references are incorporated herein by reference). General reviews of "humanized" chimeric antibodies are provided by Morrison, (*Science,* 229:1202-1207 (1985)) and by Oi, et al., *BioTechniques* 4:214 (1986); the disclosures of which are incorporated herein by reference in their entireties).

Suitable "humanized" antibodies can be alternatively produced by CDR or CEA substitution (Jones, et al., *Nature* 321:552-525 (1986); Verhoeyan et al., *Science* 239:1534 (1988); Bsidler, et al., *J. Immunol.* 141:4053-4060 (1988); the disclosures of which are incorporated herein by reference in their entireties.

Small Molecules

Screening Chemical Libraries

Having identified the interaction between Survivin and HBXIP as involved in the inhibition of apoptosis, the present invention further contemplates the use of these expressed target proteins in assays to screen libraries of compounds for candidates molecules that inhibit the interaction between Survivin and HBXIP. The generation of chemical libraries is well known in the art. A combinatorial chemical library is a collection of diverse chemical compounds generated by either chemical synthesis or biological synthesis by combining a number of chemical "building block" reagents. For example, a linear combinatorial chemical library such as a polypeptide library is formed by combining amino acids in every possible combination to yield peptides of a given length. Millions of chemical compounds theoretically can be synthesized through such combinatorial mixings of chemical building blocks. For example, one commentator observed that the systematic, combinatorial mixing of 100 interchangeable chemical building blocks results in the theoretical synthesis of 100 million tetrameric compounds or 10 billion pentameric compounds. (Gallop et al., Journal of Medicinal Chemistry, Vol. 37, No. 9, 1233-1250 (1994). Other chemical libraries known to those in the art may also be used, including natural product libraries.

Once generated, combinatorial libraries can be screened for compounds that possess desirable biological properties. For example, the ability to enhance apoptosis in cancer cells would be a useful property of a compound that can function as or be developed into an anticancer drug. One mechanism by which the compound can enhance apoptosis is through the inhibition of the interaction between Survivin and HBXIP.

To illustrate the screening process, Survivin, HBXIP and chemical compounds of the library are combined and permitted to interact with one another in the presence of pro-Caspase-9. The activation of pro-Caspase-9 is measured in the presence of Survivin, HBXIP and the candidate chemical compound. This activation is compared with the activation of pro-Caspase-9 that is measured in the presence Survivin and HBXIP without the candidate chemical compound. If the candidate compound inhibits the interaction between Survivin and HBXIP, the amount of activation of pro-Caspase-9 will increase compared to the amount pro-Caspase-9 activation in the presence of Survivin and HBXIP without candidate compound. The characteristics of each library compound are encoded so that compounds demonstrating activity that prevents or otherwise disrupts the interaction between Survivin and HBXIP can be analyzed and features common to the various compounds identified can be isolated and combined into future iterations of libraries.

Once a library of compounds is screened, subsequent libraries are generated using those chemical building blocks that possess the features shown in the first round of screening to have activity that prevents or otherwise disrupts the interaction between Survivin and HBXIP. Using this method, subsequent iterations of candidate compounds will possess more and more of those structural and functional features necessary to prevent or otherwise disrupt the interaction between Survivin and HBXIP, until a group of compounds with the ability to substantially inhibit the interaction between Survivin and HBXIP.

It will be appreciated that in addition to small molecule libraries, libraries of other compounds, such as antibodies, peptides, nucleic acids and other molecules described herein, can be used to identify compounds which inhibit the interaction between Survivin and HBXIP.

Pharmaceutical Compositions

Some embodiments of the present invention also include pharmaceutical compositions and formulations which comprise the therapeutic compounds described herein (that is, the antisense nucleic acids, catalytic RNAs, siRNAs, antibodies, peptides, peptidomimetics, small molecules and other compounds which inhibit or enhance the interaction of Survivin and HBXIP). Such pharmaceutical compositions may be administered in a number of ways depending upon whether local or systemic treatment is desired and upon the area to be treated. Administration may be topical (including ophthalmic and to mucous membranes including vaginal and rectal delivery), pulmonary, e.g., by inhalation or insufflation of powders or aerosols, including by nebulizer; intratracheal, intranasal, epidermal and transdermal), oral or parenteral. Parenteral administration includes intravenous, intraarterial, subcutaneous, intraperitoneal or intramuscular injection or infusion; or intracranial, e.g., intrathecal or intraventricular, administration.

Pharmaceutical compositions and formulations for topical administration may include transdermal patches, ointments, lotions, creams, gels, drops, suppositories, sprays, liquids and powders. Conventional pharmaceutical carriers, aqueous, powder or oily bases, thickeners and the like may be desirable. In some embodiments, topical formulations include those in which the therapeutic compounds described herein are in admixture with a topical delivery agent such as lipids, liposomes, fatty acids, fatty acid esters, steroids, chelating agents and surfactants. Exemplary lipids and liposomes include neutral (e.g. dioleoylphosphatidyl DOPE ethanolamine, dimyristoylphosphatidyl choline DMPC, distearoylphosphatidyl choline) negative (e.g. dimyristoylphosphatidyl glycerol DMPG) and cationic (e.g. dioleoyltetramethylaminopropyl DOTAP and dioleoylphosphatidyl ethanolamine DOTMA). Therapeutic compounds described herein may be encapsulated within liposomes or may form complexes thereto, in particular to cationic liposomes. Alternatively, the therapeutic compounds described herein can be complexed to lipids, in particular to cationic lipids. Preferred fatty acids and esters include but are not limited arachidonic acid, oleic acid, eicosanoic acid, lauric acid, caprylic acid, capric acid, myristic acid, palmitic acid, stearic acid, linoleic acid, linolenic acid, dicaprate, tricaprate, monoolein, dilaurin, glyceryl 1-monocaprate, 1-dodecylazacycloheptan-2-one, an acylcarnitine, an acylcholine, or a $C_{1-10}$ alkyl ester (for example, isopropylmyristate, IPM), monoglyceride, diglyceride or pharmaceutically acceptable salt thereof.

Compositions and formulations for oral administration include powders or granules, microparticulates, nanoparticulates, suspensions or solutions in water or non-aqueous media, capsules, gel capsules, sachets, tablets or minitablets. Thickeners, flavoring agents, diluents, emulsifiers, dispersing aids or binders may be desirable. In some embodiments, oral formulations are those in which the therapeutic compounds described herein are administered in conjunction with one or more penetration enhancers surfactants and chelators. In certain embodiments, surfactants include fatty acids and/or esters or salts thereof, bile acids and/or salts thereof. Exemplary bile acids/salts include chenodeoxycholic acid (CDCA) and ursodeoxychenodeoxycholic acid (UDCA), cholic acid, dehydrocholic acid, deoxycholic acid, glucholic acid, glycholic acid, glycodeoxycholic acid, taurocholic acid, taurodeoxycholic acid, sodium tauro-24,25-dihydro-fusidate, sodium glycodihydrofusidate. Exemplary fatty acids include arachidonic acid, undecanoic acid, oleic acid, lauric acid, caprylic acid, capric acid, myristic acid, palmitic acid, stearic acid, linoleic acid, linolenic acid, dicaprate, tricaprate, monoolein, dilaurin, glyceryl 1-monocaprate, I-dodecylazacycloheptan-2-one, an acylcarnitine, an acylcholine, or a monoglyceride, a diglyceride or a pharmaceutically acceptable salt thereof (for example, sodium). Some embodiments include combinations of penetration enhancers, for example, fatty acids/salts in combination with bile acids/salts. Another exemplary combination is the sodium salt of lauric acid, capric acid and UDCA. Further penetration enhancers include polyoxyethylene-9-lauryl ether, polyoxyethylene-20-cety-1 ether. The therapeutic compounds described herein can be delivered orally in granular form including sprayed dried particles, or complexed to form micro or nanoparticles. Complexing agents include poly-amino acids; polyimines; polyacrylates; polyalkylacrylates, polyoxethanes, polyalkylcyanoacrylates; cationized gelatins, albumins, starches, acrylates, polyethyleneglycols (PEG) and starches; polyalkylcyanoacrylates; DEAE-derivatized polyimines, pollulans, celluloses and starches. Other exemplary complexing agents include chitosan, N-trimethylchitosan, poly-L-lysine, polyhistidine, polyornithine, polyspermines, protamine, polyvinylpyridine, polythiodiethylamino-methylethylene P(TDAE), polyaminostyrene (e.g. p-amino), poly(methylcyanoacrylate), poly(ethylcyanoacrylate), poly(butylcyanoacrylate), poly(isobutylcyanoacrylate), poly(isohexylcynaoacrylate), DEAE-methacrylate, DEAE-hexylacrylate, DEAE-acrylamide, DEAE-albumin and DEAE-dextran, polymethylacrylate, polyhexylacrylate, poly(D,L-lactic acid), poly(DL-lactic-co-glycolic acid (PLGA), alginate, and polyethyleneglycol (PEG).

Compositions and formulations for parenteral, intrathecal or intraventricular administration of the therapeutic compounds described herein can include sterile aqueous solutions which may also contain buffers, diluents and other suitable additives such as, but not limited to, penetration enhancers, carrier compounds and other pharmaceutically acceptable carriers or excipients.

In some embodiments of the present invention, pharmaceutical compositions include, but are not limited to, solutions, emulsions, and liposome-containing formulations. These compositions may be generated from a variety of components that include, but are not limited to, preformed liquids, self-emulsifying solids and self-emulsifying semisolids.

In some embodiments of the present invention, pharmaceutical formulations, which may conveniently be presented in unit dosage form, may be prepared according to conventional techniques well known in the pharmaceutical industry. Such techniques include the step of bringing into association the active ingredients with the pharmaceutical carrier(s) or excipient(s). In general the formulations are prepared by uniformly and intimately bringing into association the active ingredients with liquid carriers or finely divided solid carriers or both, and then, if necessary, shaping the product.

The compositions of the present invention may be formulated into any of many possible dosage forms such as, but not limited to, tablets, capsules, gel capsules, liquid syrups, soft gels, suppositories, and enemas. The compositions of the present invention may also be formulated as suspensions in aqueous, non-aqueous or mixed media. Aqueous suspensions may further contain substances which increase the viscosity of the suspension including, for example, sodium carboxymethylcellulose, sorbitol and/or dextran. The suspension may also contain stabilizers.

In one embodiment of the present invention the pharmaceutical compositions may be formulated and used as foams. Pharmaceutical foams include formulations such as, but not limited to, emulsions, microemulsions, creams, jellies and liposomes. While basically similar in nature these formulations vary in the components and the consistency of the final product. The preparation of such compositions and formulations is generally known to those skilled in the pharmaceutical and formulation arts and may be applied to the formulation of the compositions of the present invention.

Emulsions

In some embodiments of the present invention, pharmaceutical compositions may be prepared and formulated as emulsions. Emulsions are typically heterogenous systems of one liquid dispersed in another in the form of droplets usually exceeding 0.1 μm in diameter. (Idson, in Pharmaceutical Dosage Forms, Lieberman, Rieger and Banker (Eds.), 1988, Marcel Dekker, Inc., New York, N.Y., volume 1, p. 199; Rosoff, in Pharmaceutical Dosage Forms, Lieberman, Rieger and Banker (Eds.), 1988, Marcel Dekker, Inc., New York, N.Y., Volume 1, p. 245; Block in Pharmaceutical Dosage Forms, Lieberman, Rieger and Banker (Eds.), 1988, Marcel Dekker, Inc., New York, N.Y., volume 2, p. 335; Higuchi et al., in Remington's Pharmaceutical Sciences, Mack Publishing Co., Easton, Pa., 1985, p. 301). Emulsions are often biphasic systems comprising of two immiscible liquid phases intimately mixed and dispersed with each other. In general, emulsions may be either water-in-oil (w/o) or of the oil-in-water (o/w) variety. When an aqueous phase is finely divided into and dispersed as minute droplets into a bulk oily phase the resulting composition is called a water-in-oil (w/o) emulsion. Alternatively, when an oily phase is finely divided into and dispersed as minute droplets into a bulk aqueous phase the resulting composition is called an oil-in-water (o/w) emulsion. Emulsions may contain additional components in addition to the dispersed phases and the active drug which may be present as a solution in either the aqueous phase, oily phase or itself as a separate phase. Pharmaceutical excipients such as emulsifiers, stabilizers, dyes, and anti-oxidants may also be present in emulsions as needed. Pharmaceutical emulsions may also be multiple emulsions that are comprised of more than two phases such as, for example, in the case of oil-in-water-in-oil (o/w/o) and water-in-oil-in-water (w/o/w) emulsions. Such complex formulations often provide certain advantages that simple binary emulsions do not. Multiple emulsions in which individual oil droplets of an o/w emulsion enclose small water droplets constitute a w/o/w emulsion. Likewise a system of oil droplets enclosed in globules of water stabilized in an oily continuous provides an o/w/o emulsion.

Emulsions are characterized by little or no thermodynamic stability. Often, the dispersed or discontinuous phase of the emulsion is well dispersed into the external or continuous phase and maintained in this form through the means of emulsifiers or the viscosity of the formulation. Either of the phases of the emulsion may be a semisolid or a solid, as is the case of emulsion-style ointment bases and creams. Other means of stabilizing emulsions entail the use of emulsifiers that may be incorporated into either phase of the emulsion. Emulsifiers may broadly be classified into four categories: synthetic surfactants, naturally occurring emulsifiers, absorption bases, and finely dispersed solids (Idson, in Pharmaceutical Dosage Forms, Lieberman, Rieger and Banker (Eds.), 1988, Marcel Dekker, Inc., New York, N.Y., volume 1, p. 199).

Synthetic surfactants, also known as surface active agents, have found wide applicability in the formulation of emulsions and have been reviewed in the literature (Rieger, in Pharmaceutical Dosage Forms, Lieberman, Rieger and Banker (Eds.), 1988, Marcel Dekker, Inc., New York, N.Y., volume 1, p. 285; Idson, in Pharmaceutical Dosage Forms, Lieberman, Rieger and Banker (Eds.), Marcel Dekker, Inc., New York, N.Y., 1988, volume 1, p. 199). Surfactants are typically amphiphilic and comprise a hydrophilic and a hydrophobic portion. The ratio of the hydrophilic to the hydrophobic nature of the surfactant has been termed the hydrophile/lipophile balance (HLB) and is a valuable tool in categorizing and selecting surfactants in the preparation of formulations. Surfactants may be classified into different classes based on the nature of the hydrophilic group: nonionic, anionic, cationic and amphoteric (Rieger, in Pharmaceutical Dosage Forms, Lieberman, Rieger and Banker (Eds.), 1988, Marcel Dekker, Inc., New York, N.Y., volume 1, p. 285).

Naturally occurring emulsifiers used in emulsion formulations include lanolin, beeswax, phosphatides, lecithin and acacia. Absorption bases possess hydrophilic properties such that they can soak up water to form w/o emulsions yet retain their semisolid consistencies, such as anhydrous lanolin and hydrophilic petrolatum. Finely divided solids have also been used as good emulsifiers especially in combination with surfactants and in viscous preparations. These include polar inorganic solids, such as heavy metal hydroxides, nonswelling clays such as bentonite, attapulgite, hectorite, kaolin, montmorillonite, colloidal aluminum silicate and colloidal magnesium aluminum silicate, pigments and nonpolar solids such as carbon or glyceryl tristearate.

A large variety of non-emulsifying materials are also included in emulsion formulations and contribute to the properties of emulsions. These include fats, oils, waxes, fatty acids, fatty alcohols, fatty esters, humectants, hydrophilic colloids, preservatives and antioxidants (Block, in Pharmaceutical Dosage Forms, Lieberman, Rieger and Banker (Eds.), 1988, Marcel Dekker, Inc., New York, N.Y., volume 1, p. 335; Idson, in Pharmaceutical Dosage Forms, Lieberman, Rieger and Banker (Eds.), 1988, Marcel Dekker, Inc., New York, N.Y., volume 1, p. 199).

Hydrophilic colloids or hydrocolloids include naturally occurring gums and synthetic polymers such as polysaccharides (for example, acacia, agar, alginic acid, carrageenan, guar gum, karaya gum, and tragacanth), cellulose derivatives (for example, carboxymethylcellulose and carboxypropylcellulose), and synthetic polymers (for example, carbomers, cellulose ethers, and carboxyvinyl polymers). These disperse or swell in water to form colloidal solutions that stabilize emulsions by forming strong interfacial films around the dispersed-phase droplets and by increasing the viscosity of the external phase.

Since emulsions often contain a number of ingredients such as carbohydrates, proteins, sterols and phosphatides that may readily support the growth of microbes, these formulations often incorporate preservatives. Commonly used preservatives included in emulsion formulations include methyl paraben, propyl paraben, quaternary ammonium salts, benzalkonium chloride, esters of p-hydroxybenzoic acid, and boric acid. Antioxidants are also commonly added to emulsion formulations to prevent deterioration of the formulation. Antioxidants used may be free radical scavengers such as tocopherols, alkyl gallates, butylated hydroxyanisole, butylated hydroxytoluene, or reducing agents such as ascorbic acid and sodium metabisulfite, and antioxidant synergists such as citric acid, tartaric acid, and lecithin.

The application of emulsion formulations via dermatological, oral and parenteral routes and methods for their manufacture have been reviewed in the literature (Idson, in Pharmaceutical Dosage Forms, Lieberman, Rieger and Banker (Eds.), 1988, Marcel Dekker, Inc., New York, N.Y., volume 1, p. 199). Emulsion formulations for oral delivery have been very widely used because of reasons of ease of formulation, efficacy from an absorption and bioavailability standpoint. (Rosoff, in Pharmaceutical Dosage Forms, Lieberman, Rieger and Banker (Eds.), 1988, Marcel Dekker, Inc., New York, N.Y., volume 1, p. 245; Idson, in Pharmaceutical Dosage Forms, Lieberman, Rieger and Banker (Eds.), 1988, Marcel Dekker, Inc., New York, N.Y., volume 1, p. 199). Mineral-oil base laxatives, oil-soluble vitamins and high fat nutritive preparations are among the materials that have commonly been administered orally as o/w emulsions.

In one embodiment of the present invention, a pharmaceutical composition comprising a therapeutic compound described herein is formulated as a microemulsion. A microemulsion may be defined as a system of water, oil and amphiphile which is a single optically isotropic and thermodynamically stable liquid solution (Rosoff, in Pharmaceutical Dosage Forms, Lieberman, Rieger and Banker (Eds.), 1988, Marcel Dekker, Inc., New York, N.Y., volume 1, p. 245). Typically microemulsions are systems that are prepared by first dispersing an oil in an aqueous surfactant solution and then adding a sufficient amount of a fourth component, generally an intermediate chain-length alcohol to form a transparent system. Therefore, microemulsions have also been described as thermodynamically stable, isotropically clear dispersions of two immiscible liquids that are stabilized by interfacial films of surface-active molecules (Leung and Shah, in: Controlled Release of Drugs: Polymers and Aggregate Systems, Rosoff, M., Ed., 1989, VCH Publishers, New York, pages 185-215). Microemulsions commonly are prepared via a combination of three to five components that include oil, water, surfactant, cosurfactant and electrolyte. Whether the microemulsion is of the water-in-oil (w/o) or an oil-in-water (o/w) type is dependent on the properties of the oil and surfactant used and on the structure and geometric packing of the polar heads and hydrocarbon tails of the surfactant molecules (Schott, in Remington's Pharmaceutical Sciences, Mack Publishing Co., Easton, Pa., 1985, p. 271).

The phenomenological approach utilizing phase diagrams has been extensively studied and has yielded a comprehensive knowledge, to one skilled in the art, of how to formulate microemulsions (Rosoff, in Pharmaceutical Dosage Forms, Lieberman, Rieger and Banker (Eds.), 1988, Marcel Dekker, Inc., New York, N.Y., volume 1, p. 245; Block, in Pharmaceutical Dosage Forms, Lieberman, Rieger and Banker (Eds.), 1988, Marcel Dekker, Inc., New York, N.Y., volume 1, p. 335). Compared to conventional emulsions, microemulsions offer the advantage of solubilizing water-insoluble drugs in a formulation of thermodynamically stable droplets that are formed spontaneously. Surfactants used in the preparation of microemulsions include, but are not limited to, ionic surfactants, non-ionic surfactants, Brij 96, polyoxyethylene oleyl ethers, polyglycerol fatty acid esters, tetraglycerol monolaurate (ML310), tetraglycerol monooleate (MO310), hexaglycerol monooleate (PO310), hexaglycerol pentaoleate (PO500), decaglycerol monocaprate (MCA750), decaglycerol monooleate (MO750), decaglycerol sequioleate (SO750), decaglycerol decaoleate (DAO750), alone or in combination with cosurfactants. The cosurfactant, usually a short-chain alcohol such as ethanol, 1-propanol, and 1-butanol, serves to increase the interfacial fluidity by penetrating into the surfactant film and consequently creating a disordered film because of the void space generated among surfactant molecules. Microemulsions may, however, be prepared without the use of cosurfactants and alcohol-free self-emulsifying microemulsion systems are known in the art. The aqueous phase may typically be, but is not limited to, water, an aqueous solution of the drug, glycerol, PEG300, PEG400, polyglycerols, propylene glycols, and derivatives of ethylene glycol. The oil phase may include, but is not limited to, materials such as Captex 300, Captex 355, Capmul MCM, fatty acid esters, medium chain (C8-C12) mono, di, and triglycerides, polyoxyethylated glyceryl fatty acid esters, fatty alcohols, polyglycolized glycerides, saturated polyglycolized C8-C10 glycerides, vegetable oils and silicone oil.

Microemulsions are particularly of interest from the standpoint of drug solubilization and the enhanced absorption of drugs. Lipid based microemulsions (both o/w and w/o) have been proposed to enhance the oral bioavailability of drugs, including peptides (Constantinides et al., Pharmaceutical Research, 1994, 11, 1385-1390; Ritschel, Meth. Find. Exp. Clin. Pharmacol., 1993, 13, 205). Microemulsions afford advantages of improved drug solubilization, protection of drug from enzymatic hydrolysis, possible enhancement of drug absorption due to surfactant-induced alterations in membrane fluidity and permeability, ease of preparation, ease of oral administration over solid dosage forms, improved clinical potency, and decreased toxicity (Constantinides et al., Pharmaceutical Research, 1994, 11, 1385; Ho et al., J. Pharm. Sci., 1996, 85, 138-143). Often microemulsions may form spontaneously when their components are brought together at ambient temperature. This may be particularly advantageous when formulating thermolabile drugs, peptides or oligonucleotides. Microemulsions have also been effective in the transdermal delivery of active components in both cosmetic and pharmaceutical applications. It is expected that the microemulsion compositions and formulations of the present invention will facilitate the increased systemic absorption of oligonucleotides and nucleic acids from the gastrointestinal tract, as well as improve the local cellular uptake of oligonucleotides and nucleic acids within the gastrointestinal tract, vagina, buccal cavity and other areas of administration.

In some embodiments of the present invention, microemulsions can also contain additional components and additives such as sorbitan monostearate (Grill 3), Labrasol, and penetration enhancers to improve the properties of the formulation and to enhance the absorption of the therapeutic compounds described herein. Penetration enhancers used in the microemulsions can be classified as belonging to one of five broad categories—surfactants, fatty acids, bile salts, chelating agents, and non-chelating non-surfactants (Lee et al., Critical Reviews in Therapeutic Drug Carrier Systems, 1991, p. 92). Each of these classes has been discussed above.

Liposomes

There are many organized surfactant structures besides microemulsions that have been studied and used for the formulation of drugs. These include monolayers, micelles, bilayers and vesicles. Vesicles, such as liposomes, have attracted great interest because of their specificity and the duration of action they offer from the standpoint of drug delivery. As used herein, the term "liposome" means a vesicle composed of amphiphilic lipids arranged in a spherical bilayer or bilayers.

Liposomes are unilamellar or multilamellar vesicles which have a membrane formed from a lipophilic material and an aqueous interior. The aqueous portion contains the composition to be delivered. Cationic liposomes possess the advantage of being able to fuse to the cell wall. Non-cationic liposomes, although not able to fuse as efficiently with the cell wall, are taken up by macrophages in vivo.

In order to cross intact mammalian skin, lipid vesicles must pass through a series of fine pores, each with a diameter less than 50 nm, under the influence of a suitable transdermal gradient. Therefore, it is desirable to use a liposome which is highly deformable and able to pass through such fine pores.

Further advantages of liposomes include, but are not limited to, the following: (1) liposomes obtained from natural phospholipids are biocompatible and biodegradable; (2) liposomes can incorporate a wide range of water and lipid soluble drugs; and (3) liposomes can protect encapsulated drugs in their internal compartments from metabolism and degradation (Rosoff, in Pharmaceutical Dosage Forms, Lieberman, Rieger and Banker (Eds.), 1988, Marcel Dekker, Inc., New York, N.Y., volume 1, p. 245). Important considerations in the preparation of liposome formulations are the lipid surface charge, vesicle size and the aqueous volume of the liposomes.

Liposomes are useful for the transfer and delivery of active ingredients to the site of action. Because the liposomal membrane is structurally similar to biological membranes, when liposomes are applied to a tissue, the liposomes start to merge with the cellular membranes. As the merging of the liposome and cell progresses, the liposomal contents are emptied into the cell where the active agent may act.

Liposomal formulations have been the focus of extensive investigation as the mode of delivery for many drugs. There is growing evidence that for topical administration, liposomes present several advantages over other formulations. Such advantages include reduced side-effects related to high systemic absorption of the administered drug, increased accumulation of the administered drug at the desired target, and the ability to administer a wide variety of drugs, both hydrophilic and hydrophobic, into the skin.

Several reports have detailed the ability of liposomes to deliver into the skin agents ranging from the size of small molecules to high-molecular weight DNA. Compounds including analgesics, antibodies, hormones and high-molecular weight DNAs have been administered to the skin. The majority of applications result in the targeting of the upper epidermis.

Liposomes fall into two broad classes. Cationic liposomes are positively charged liposomes which interact with the negatively charged DNA molecules to form a stable complex. The positively charged DNA/liposome complex binds to the negatively charged cell surface and is internalized in an endosome. Due to the acidic pH within the endosome, the liposomes are ruptured, releasing their contents into the cell cytoplasm (Wang et al., Biochem. Biophys. Res. Commun., 1987, 147, 980-985).

Liposomes which are pH-sensitive or negatively-charged, entrap molecules rather than complex with them. pH-sensitive liposomes have been used to deliver various types of molecules to cells in experimental animals and cells in culture.

One major type of liposomal composition includes phospholipids other than naturally-derived phosphatidylcholine. Neutral liposome compositions, for example, can be formed from dimyristoyl phosphatidylcholine (DMPC) or dipalmitoyl phosphatidylcholine (DPPC). Anionic liposome compositions generally are formed from dimyristoyl phosphatidylglycerol, while anionic fusogenic liposomes are formed primarily from dioleoyl phosphatidylethanolamine (DOPE). Another type of liposomal composition is formed from phosphatidylcholine (PC) such as, for example, soybean PC, and egg PC. Another type is formed from mixtures of phospholipid and/or phosphatidylcholine and/or cholesterol.

Several studies have assessed the topical delivery of liposomal drug formulations to the skin. Application of liposomes containing interferon to guinea pig skin resulted in a reduction of skin herpes sores while delivery of interferon via other means (e.g. as a solution or as an emulsion) were ineffective (Weiner et al., Journal of Drug Targeting, 1992, 2, 405-410). Further, an additional study tested the efficacy of interferon administered as part of a liposomal formulation to the administration of interferon using an aqueous system, and concluded that the liposomal formulation was superior to aqueous administration (du Plessis et al., Antiviral Research, 1992, 18, 259-265).

Non-ionic liposomal systems have also been examined to determine their utility in the delivery of drugs to the skin, in particular systems comprising non-ionic surfactant and cholesterol. Non-ionic liposomal formulations comprising Novasome™ I (glyceryl dilaurate/cholesterol/po-lyoxyethylene-10-stearyl ether) and Novasome™ II (glyceryl distearate/cholesterol/polyoxyethylene-10-stearyl ether) were used to deliver cyclosporin-A into the dermis of mouse skin. Results indicated that such non-ionic liposomal systems were effective in facilitating the deposition of cyclosporin-A into different layers of the skin (Hu et al. S. T. P. Pharma. Sci., 1994, 4, 6, 466).

Liposomes also include "sterically stabilized" liposomes, a term which, as used herein, refers to liposomes comprising one or more specialized lipids that, when incorporated into liposomes, result in enhanced circulation lifetimes relative to liposomes lacking such specialized lipids. Examples of sterically stabilized liposomes are those in which part of the vesicle-forming lipid portion of the liposome (A) comprises one or more glycolipids, such as monosialoganglioside $G_{M1}$, or (B) is derivatized with one or more hydrophilic polymers, such as a polyethylene glycol (PEG) moiety. While not wishing to be bound by any particular theory, it is thought in the art that, at least for sterically stabilized liposomes containing gangliosides, sphingomyelin, or PEG-derivatized lipids, the enhanced circulation half-life of these sterically stabilized liposomes derives from a reduced uptake into cells of the reticuloendothelial system (RES) (Allen et al., FEBS Letters, 1987, 223, 42; Wu et al., Cancer Research, 1993, 53, 3765).

Various liposomes comprising one or more glycolipids are known in the art. Papahadjopoulos et al. (Ann. N.Y. Acad. Sci., 1987, 507, 64) reported the ability of monosialoganglioside $G_{M1}$, galactocerebroside sulfate and phosphatidylinositol to improve blood half-lives of liposomes. These findings were expounded upon by Gabizon et al. (Proc. Natl. Acad. Sci. U.S.A., 1988, 85, 6949). U.S. Pat. No. 4,837,028 and WO 88/04924, both to Allen et al., disclose liposomes comprising (1) sphingomyelin and (2) the ganglioside $G_{M1}$ or a galactocerebroside sulfate ester. U.S. Pat. No. 5,543,152 (Webb et al.) discloses liposomes comprising sphingomyelin. Liposomes comprising 1,2-sn-dimyristoylphosphat-idylcholine are disclosed in WO 97/13499 (Lim et al.).

Many liposomes comprising lipids derivatized with one or more hydrophilic polymers, and methods of preparation thereof, are known in the art. Sunamoto et al. (Bull. Chem. Soc. Jpn., 1980, 53, 2778) described liposomes comprising a nonionic detergent, 2C.sub.1215G, that contains a PEG moiety. Illum et al. (FEBS Lett., 1984, 167, 79) noted that hydrophilic coating of polystyrene particles with polymeric glycols results in significantly enhanced blood half-lives. Synthetic phospholipids modified by the attachment of carboxylic groups of polyalkylene glycols (e.g., PEG) are described by Sears (U.S. Pat. Nos. 4,426,330 and 4,534,899). Klibanov et al. (FEBS Lett., 1990, 268, 235) described experiments demonstrating that liposomes comprising phosphatidylethanolamine (PE) derivatized with PEG or PEG stearate have significant increases in blood circulation half-lives. Blurne et al. (Biochimica et Biophysica Acta, 1990, 1029, 91) extended such observations to other PEG-derivatized phospholipids, e.g., DSPE-PEG, formed from the combination of distearoylphosphatidylethanolamine (DSPE) and PEG. Liposomes having covalently bound PEG moieties on their external surface are described in European Patent No. PP 0 445 131 B1 and WO 90/04384 to Fisher. Liposome compositions containing 1-20 mole percent of PE derivatized with PEG, and methods of use thereof, are described by Woodle et al. (U.S. Pat. Nos. 5,013,556 and 5,356,633) and Martin et al. (U.S. Pat. No. 5,213,804 and European Patent No. EP 0 496 813 B1). Liposomes comprising a number of other lipid-polymer conjugates are disclosed in WO 91/05545 and U.S. Pat. No. 5,225,212 (both to Martin et al.) and in WO 94/20073 (Zalipsky et al.) Liposomes comprising PEG-modified ceramide lipids are described in WO 96/10391 (Choi et al.). U.S. Pat. Nos. 5,540,935 (Miyazaki et al.) and 5,556,948 (Tagawa et al.) describe PEG-containing liposomes that can be further derivatized with functional moieties on their surfaces.

Transfersomes are yet another type of liposomes, and are highly deformable lipid aggregates which are attractive candidates for drug delivery vehicles. Transfersomes may be described as lipid droplets which are so highly deformable that they are easily able to penetrate through pores which are smaller than the droplet. Transfersomes are adaptable to the environment in which they are used, e.g. they are self-optimizing (adaptive to the shape of pores in the skin), self-repairing, frequently reach their targets without fragmenting, and often self-loading. To make transfersomes it is possible to add surface edge-activators, usually surfactants, to a standard liposomal composition. Transfersomes have been used to deliver serum albumin to the skin. The transfersome-mediated delivery of serum albumin has been shown to be as effective as subcutaneous injection of a solution containing serum albumin.

Surfactants find wide application in formulations such as emulsions (including microemulsions) and liposomes. The most common way of classifying and ranking the properties of the many different types of surfactants, both natural and synthetic, is by the use of the hydrophile/lipophile balance (HLB). The nature of the hydrophilic group (also known as the "head") provides the most useful means for categorizing the different surfactants used in formulations (Rieger, in Pharmaceutical Dosage Forms, Marcel Dekker, Inc., New York, N.Y., 1988, p. 285).

If the surfactant molecule is not ionized, it is classified as a nonionic surfactant. Nonionic surfactants find wide application in pharmaceutical and cosmetic products and are usable over a wide range of pH values. In general their HLB values range from 2 to about 18 depending on their structure. Nonionic surfactants include nonionic esters such as ethylene glycol esters, propylene glycol esters, glyceryl esters, polyglyceryl esters, sorbitan esters, sucrose esters, and ethoxylated esters. Nonionic alkanolamides and ethers such as fatty alcohol ethoxylates, propoxylated alcohols, and ethoxylated/propoxylated block polymers are also included in this class. The polyoxyethylene surfactants are the most popular members of the nonionic surfactant class.

If the surfactant molecule carries a negative charge when it is dissolved or dispersed in water, the surfactant is classified as anionic. Anionic surfactants include carboxylates such as soaps, acyl lactylates, acyl amides of amino acids, esters of sulfuric acid such as alkyl sulfates and ethoxylated alkyl sulfates, sulfonates such as alkyl benzene sulfonates, acyl isethionates, acyl taurates and sulfosuccinates, and phosphates. The most important members of the anionic surfactant class are the alkyl sulfates and the soaps.

If the surfactant molecule carries a positive charge when it is dissolved or dispersed in water, the surfactant is classified as cationic. Cationic surfactants include quaternary ammonium salts and ethoxylated amines. The quaternary ammonium salts are the most used members of this class.

If the surfactant molecule has the ability to carry either a positive or negative charge, the surfactant is classified as amphoteric. Amphoteric surfactants include acrylic acid derivatives, substituted alkylamides, N-alkylbetaines and phosphatides.

The use of surfactants in drug products, formulations and in emulsions has been reviewed (Rieger, in Pharmaceutical Dosage Forms, Marcel Dekker, Inc., New York, N.Y., 1988, p. 285).

Penetration Enhancers

In one embodiment, the present invention employs various penetration enhancers to effect the efficient delivery of the therapeutic compounds described herein, to the skin of animals. Most drugs are present in solution in both ionized and nonionized forms. However, usually only lipid soluble or lipophilic drugs readily cross cell membranes. It has been discovered that even non-lipophilic drugs may cross cell membranes if the membrane to be crossed is treated with a penetration enhancer. In addition to aiding the diffusion of non-lipophilic drugs across cell membranes, penetration enhancers also enhance the permeability of lipophilic drugs.

Penetration enhancers may be classified as belonging to one of five broad categories, i.e., surfactants, fatty acids, bile salts, chelating agents, and non-chelating non-surfactants (Lee et al., Critical Reviews in Therapeutic Drug Carrier Systems, 1991, p. 92). Each of the above mentioned classes of penetration enhancers are described below in greater detail.

Surfactants: In connection with the present invention, surfactants (or "surface-active agents") are chemical entities which, when dissolved in an aqueous solution, reduce the surface tension of the solution or the interfacial tension between the aqueous solution and another liquid, with the result that absorption of oligonucleotides through the mucosa is enhanced. In addition to bile salts and fatty acids, these penetration enhancers include, for example, sodium lauryl sulfate, polyoxyethylene-9-lauryl ether and polyoxyethylene-20-cetyl ether.

Fatty acids: Various fatty acids and their derivatives which act as penetration enhancers include, for example, oleic acid, lauric acid, capric acid (n-decanoic acid), myristic acid, palmitic acid, stearic acid, linoleic acid, linolenic acid, dicaprate, tricaprate, monoolein (1-monooleoyl-rac-glycerol), dilaurin, caprylic acid, arachidonic acid, glycerol 1-monocaprate, 1-dodecylazacycloheptan-2-one, acylcarnitines, acylcholines, C1-10 alkyl esters thereof (e.g., methyl, isopropyl and t-butyl), and mono- and di-glycerides thereof (for example, oleate, laurate, caprate, myristate, palmitate, stearate, and linoleate).

Bile salts: The physiological role of bile includes the facilitation of dispersion and absorption of lipids and fat-soluble vitamins. Various natural bile salts, and their synthetic derivatives, act as penetration enhancers. Thus the term "bile salts" includes any of the naturally occurring components of bile as well as any of their synthetic derivatives. Exemplary bile salts include, for example, cholic acid (or its pharmaceutically acceptable sodium salt, sodium cholate), dehydrocholic acid (sodium dehydrocholate), deoxycholic acid (sodium deoxycholate), glucholic acid (sodium glucholate), glycholic acid (sodium glycocholate), glycodeoxycholic acid (sodium glycodeoxycholate), taurocholic acid (sodium taurocholate), taurodeoxycholic acid (sodium taurodeoxycholate), chenodeoxycholic acid (sodium chenodeoxycholate), ursodeoxycholic acid (UDCA), sodium tauro-24,25-dihydro-fusidate (STDHF), sodium glycodihydrofusidate and polyoxyethylene-9-lauryl ether (POE).

Chelating Agents: Chelating agents, as used in connection with the therapeutic compounds described herein, can be defined as compounds that remove metallic ions from solution by forming complexes therewith. For example, the chelation of metal ions enhances the absorption of oligonucleotides through mucosa. In addition to the use of chelating agents as penetration enhancers, with respect to the nucleic acid compounds described herein, chelating agents have the added advantage of also serving as nuclease inhibitors. Exemplary chelating agents include, but are not limited to, disodium ethylenediaminetetraacetate (EDTA), citric acid, salicylates (for example, sodium salicylate, 5-methoxysalicylate and homovanilate), N-acyl derivatives of collagen, laureth-9 and N-amino acyl derivatives of beta-diketones (enamines).

Non-chelating non-surfactants: As used herein, non-chelating non-surfactant penetration enhancing compounds can be defined as compounds that demonstrate insignificant activity as chelating agents or as surfactants but that nonetheless enhance absorption of the compounds described herein through the alimentary mucosa. This class of penetration enhancers include, for example, unsaturated cyclic ureas, 1-alkyl- and 1-alkenylazacyclo-alkanone derivatives; and non-steroidal anti-inflammatory agents such as diclofenac sodium, indomethacin and phenylbutazone.

Agents that enhance uptake of oligonucleotides at the cellular level may also be added to the pharmaceutical and other compositions of the present invention. For example, cationic lipids, such as lipofectin (Junichi et al, U.S. Pat. No. 5,705,188), cationic glycerol derivatives, and polycationic molecules, such as polylysine (Lollo et al., PCT Application WO 97/30731), are also known to enhance the cellular uptake of oligonucleotides.

Other agents may be utilized to enhance the penetration of the therapeutic compounds described herein, including glycols such as ethylene glycol and propylene glycol, pyrrols such as 2-pyrrol, azones, and terpenes such as limonene and menthone.

Excipients

As used herein, a "pharmaceutical carrier" or "excipient" is a pharmaceutically acceptable solvent, suspending agent or any other pharmacologically inert vehicle for delivering one or more of the therapeutic compounds described herein. The excipient may be liquid or solid and is selected, with the planned manner of administration in mind, so as to provide for the desired bulk, consistency, etc., when combined with a therapeutic compounds described herein and the other components of a given pharmaceutical composition. Typical pharmaceutical carriers include, but are not limited to, binding agents (e.g., pregelatinized maize starch, polyvinylpyrrolidone or hydroxypropyl methylcellulose, etc.); fillers (e.g., lactose and other sugars, microcrystalline cellulose, pectin, gelatin, calcium sulfate, ethyl cellulose, polyacrylates or calcium hydrogen phosphate, etc.); lubricants (e.g., magnesium stearate, talc, silica, colloidal silicon dioxide, stearic acid, metallic stearates, hydrogenated vegetable oils, corn starch, polyethylene glycols, sodium benzoate, sodium acetate, etc.); disintegrants (e.g., starch, sodium starch glycolate, etc.); and wetting agents (e.g., sodium lauryl sulphate, etc.).

Pharmaceutically acceptable organic or inorganic excipient suitable for non-parenteral administration which do not deleteriously react with therapeutic compounds described herein can also be used to formulate the pharmaceutical compositions of the present invention. Suitable pharmaceutically acceptable carriers include, but are not limited to, water, salt solutions, alcohols, polyethylene glycols, gelatin, lactose, amylose, magnesium stearate, talc, silicic acid, viscous paraffin, hydroxymethylcellulose, polyvinylpyrrolidone and the like.

Formulations for topical administration of therapeutic compounds described herein may include sterile and non-sterile aqueous solutions, non-aqueous solutions in common solvents such as alcohols, or solutions of the nucleic acids in liquid or solid oil bases. The solutions may also contain buffers, diluents and other suitable additives. Pharmaceutically acceptable organic or inorganic excipients suitable for non-parenteral administration which do not deleteriously react with nucleic acids can be used.

Suitable pharmaceutically acceptable excipients include, but are not limited to, water, salt solutions, alcohol, polyethylene glycols, gelatin, lactose, amylose, magnesium stearate, talc, silicic acid, viscous paraffin, hydroxymethylcellulose, polyvinylpyrrolidone and the like.

Other Components

The compositions of the present invention may additionally contain other adjunct components conventionally found in pharmaceutical compositions, at their art-established usage levels. Thus, for example, the compositions may contain additional, compatible, pharmaceutically-active materials such as, for example, antipruritics, astringents, local anesthetics or anti-inflammatory agents, or may contain additional materials useful in physically formulating various dosage forms of the compositions of the present invention, such as dyes, flavoring agents, preservatives, antioxidants, opacifiers, thickening agents and stabilizers. However, such materials, when added, should not unduly interfere with the biological activities of the components of the compositions of the present invention. The formulations can be sterilized and, if desired, mixed with auxiliary agents, e.g., lubricants, preservatives, stabilizers, wetting agents, emulsifiers, salts for influencing osmotic pressure, buffers, colorings, flavorings and/or aromatic substances and the like which do not deleteriously interact with the nucleic acid(s) of the formulation.

Aqueous suspensions may contain substances which increase the viscosity of the suspension including, for example, sodium carboxymethylcellulose, sorbitol and/or dextran. The suspension may also contain stabilizers.

Dosing

Formulation of the therapeutic compounds described herein and their subsequent administration is believed to be within the skill of those in the art. Dosing is dependent on severity and responsiveness of the disease state to be treated, with the course of treatment lasting from several days to several months, or until a cure is effected or a diminution of the disease state is achieved. Optimal dosing schedules can be calculated from measurements of drug accumulation in the body of the patient. Persons of ordinary skill can easily determine optimum dosages, dosing methodologies and repetition rates. Optimum dosages may vary depending on the relative potency of individual oligonucleotides, and can generally be estimated based on $EC_{50}$ found to be effective in in vitro and in vivo animal models. In general, dosage is from 0.01 μg to 100 g per kg of body weight, and may be given once or more daily, weekly, monthly or yearly, or even once every 2 to 20 years. Persons of ordinary skill in the art can easily estimate repetition rates for dosing based on measured residence times and concentrations of the drug in bodily fluids or tissues. Following successful treatment, it may be desirable to have the patient undergo maintenance therapy to prevent the recurrence of the disease state, wherein the oligonucleotide is administered in maintenance doses, ranging from 0.01 μg to 100 g per kg of body weight, once or more daily, to once every 20 years.

Structure Activity Relationships

In some embodiments of the present invention, sites of interaction between Survivin and HBXIP are identified. Such sites can be a site on Survivin to which HBXIP binds or a site on HBXIP to which Survivin binds. These binding sites can be used as potential targets for compounds that interfere with or otherwise disrupt the interaction between Survivin and HBXIP. Sites of interaction between Survivin and HBXIP can be determined using structural biology methods including, but not limited to, nuclear magnetic resonance spectroscopy, x-ray diffraction, computer-based structural predication methods and computer-based molecular threading.

In certain embodiments of the present invention, transverse relaxation-optimized spectroscopy (TROSY) is used to determine site of interaction between Survivin and HBXIP. For example, TROSY can be used to determine binding sites for HBXIP that are present on the Survivin protein or alternatively binding sites for Survivin that are present on HBXIP. Once the three-dimensional structure of such binding sites are identified, candidate compounds that potentially have affinity for one or more of these sites can be identified then tested to determine their ability to interact with these binding sites. In addition to TROSY, other spectroscopic methods, such as cross relaxation-enhanced polarization transfer NMR (CRINEPT) can be used to determine sites of interaction between Survivin and HBXIP. The techniques of CRINEPT and TROSY have been described elsewhere such as in U.S. Pat. No. 6,396,267, the disclosure of which is incorporated herein by reference in its entirety.

In some embodiments of the present invention, methods for screening compounds using spectral techniques to determine binding of compounds to the HBXIP binding site of Survivin or to the Survivin binding site of HBXIP are contemplated. Such methods identify compounds that may be useful in altering the association of HBXIP and Survivin. Compounds may be screened by using a combination of Nuclear Magnetic Resonance (NMR) binding assays, Fluorescence Polarization Assay (FPA) and Computational-Docking studies.

Some embodiments of this invention are further illustrated by the following examples which should not be construed as limiting. It will be appreciated by those of skill in the art that the techniques disclosed in the examples which follow represent techniques discovered by the inventor to function well in the practice of the embodiments of the invention described herein, and thus can be considered to constitute preferred modes for the practice of these embodiments. Those of skill in the art will, however, in light of the present disclosure, appreciate that many changes can be made in the specific embodiments which are disclosed herein and still obtain a like or similar result without departing from the spirit and scope of the invention.

Example 1

Survivin Differs from XIAP in Caspase Inhibitory Activity

Over-expression of various IAP-family proteins can suppress Caspase activation and apoptosis induced by various stimuli. The effects of Survivin were compared with XIAP, an extensively studied IAP-family member which has been shown unequivocally to directly bind and suppress certain Caspases, including Caspases-3, 7, and 9 (Deveraux, Q. L. & Reed, J. C. 1999 *Genes Dev* 13:239-252; Deveraux, Q. L. et al. 1997 *Nature* 388:300-304; Sun, C. et al. 1999 *Nature* 401:818-821; Riedl, S. J. et al. 2001 *Cell* 104:791-800).

Primary hepatocellular carcinoma tissues and their corresponding non-cancerous regions were obtained from patients undergoing biopsy or surgery at Kyoto University Hospital after obtaining informed consent. Cytosolic extracts from cells or liver tissues were prepared in buffer A (10 mM KCl, 1.5 mM $MgCl_2$, 1 mM EDTA, 1 mM EGTA, 1 mM dithiothreitol, 0.1 mM PMSF and 20 mM HEPES-KOH pH 7.4), as described previously (Deveraux, Q. L. et al 1997 *Nature* 388:300-304). After measuring protein levels (Biorad, Hercules, Calif.), 20 μg of protein sample was incubated with either 10 nM of recombinant Caspase-8, 1 ng of Granzyme B (Calbiochem), or 10 μM of Cytochrome C and 1 mM dATP, with or without various purified proteins in Caspase Buffer (1 mM EDTA, 0.1% Chaps and 10% Sucrose and 25 mM HEPES pH 7.2). Then, 5 μl of reaction mixtures were incubated with fluorogenic caspase substrate acetyl-Asp-Glu-Val-Asp-aminofluorocoumarin (Ac-DEVD-AFC) (Calbiochem) in 100 μl Caspase buffer. Caspase activity was assayed by using a LS50B fluorometric plate reader (Perkin-Elmer, Norwalk, Conn.) in the kinetic mode with excitation and emission wavelength of 405 and 510 nm, respectively. Release of AFC from the substrate peptide was compared after 30 min incubation.

First, the effects of purified recombinant Survivin and XIAP on recombinant active Caspase-3 were compared in vitro. In contrast to XIAP, which potently suppressed Caspase-3, Survivin displayed no ability to suppress Caspase-3 protease activity, as measured by the hydrolysis of the fluorigenic peptide substrate Ac-DEVD-AFC (FIGS. 1*a* and 1*b*). Even at a 1000-fold molar excess of Survivin relative to active Caspase-3, essentially no inhibition was observed. Similar results were obtained using recombinant active Caspase-7 and -9. Again, XIAP inhibited, but Survivin did not.

Caspase activity in cell extracts was then measured, using exogenously supplied Cytochrome C to trigger activation of Caspases—a treatment which is known to cause Cytochrome C-dependent oligomerization of the Caspase-activator, Apaf1, with Apaf1 then binding and activating pro-Caspase-9, followed by cleavage and activation of downstream protease Caspase-3 (Zou, H. et al. 1999 *J Biol Chem* 274:11549-11556). When purified recombinant Survivin or XIAP was added to extracts prior to stimulation with Cytochrome C, Caspase activity in the cell lysates was suppressed in a concentration-dependent manner by both proteins (FIGS. 1*c* and 1*d*). However, if Survivin or XIAP was added to extracts after stimulation with Cytochrome C, then XIAP suppressed Caspase activity, whereas Survivin did not (FIG. 1*e* and 1*f*).

These results show that while Survivin is ineffective by itself at suppressing Caspases, in collaboration with other proteins present in cell lysates, Survivin can prevent Cytochrome C-mediated activation of Caspases. However, unlike XIAP, Survivin does not appear to inhibit Caspases in cell lysates once they have been activated.

Example 2

Identification of HBXIP as a Survivin Binding Partner

To identify potential partners of Survivin, we performed yeast two-hybrid screens of cDNA libraries using human Survivin protein as bait.

For library screening, a human Jurkat T cell cDNA library in pJG4-5 and the EGY48 strain of *Saccharomyces cerevisiae* (MAT, trp1, ura3, his, leu2:plexApo6-leu2) were used, as described (Matsuzawa, S. & Reed, J. C. 2001 *Mol Cell* 7:915-926). A cDNA encoding full-length Survivin was cloned into the EcoRI and XhoI sites of the yeast two-hybrid vector, pGilda (Clontech, Palo Alto, Calif.), which produces fusion proteins with a LexA DNA-binding domain. Specificity of interactions was confirmed by mating experiments using a panel of yeast containing various control bait-plasmids (pGilda-Bax, -Fas, -caspase-9), and by re-transformation experiments (see FIG. 7).

Figure 7:
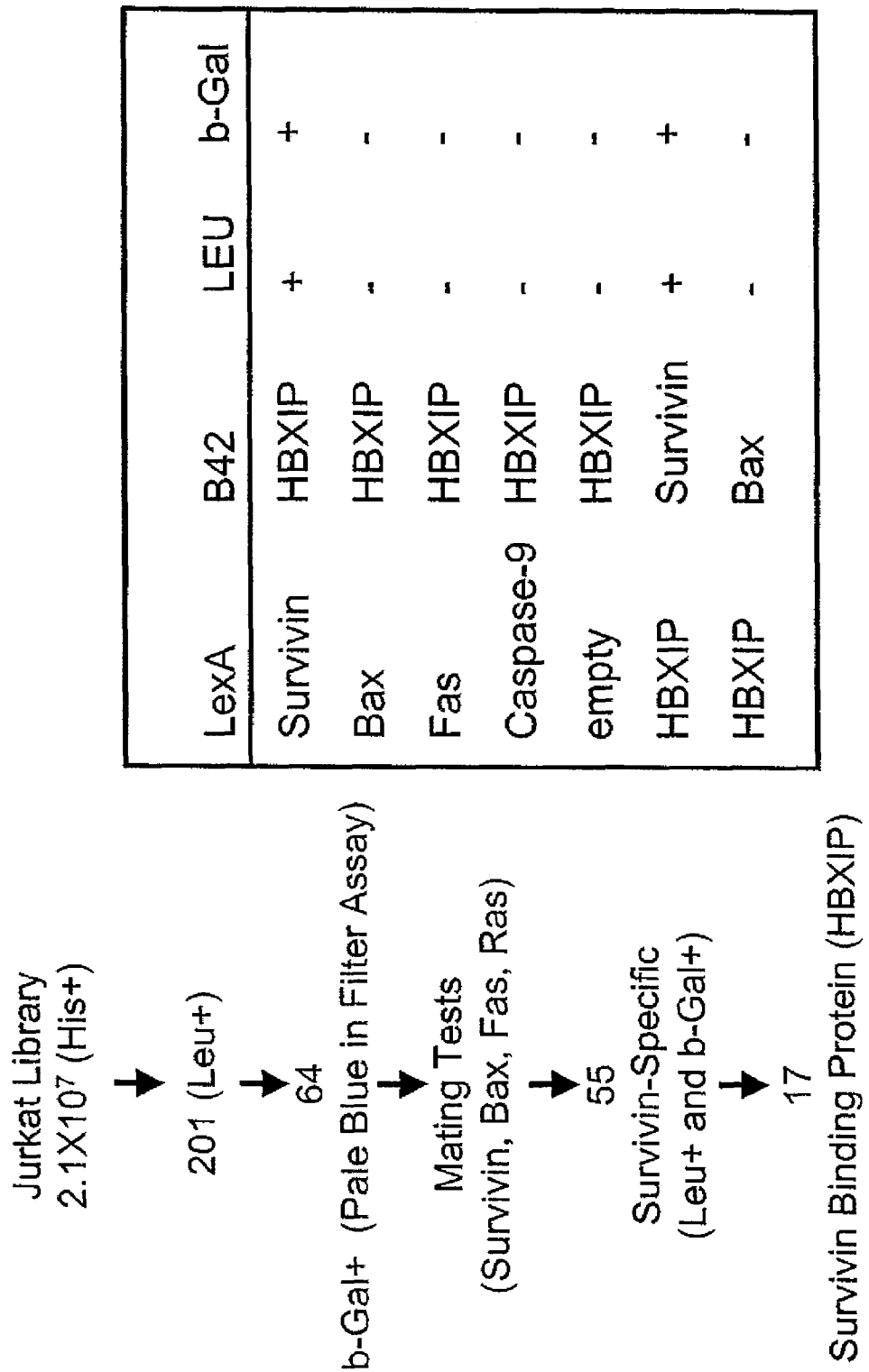
FIG. 7 shows details of yeast two-hybrid screening using human Survivin as bait.

From a pool of 64 candidate clones, 17 were found to represent cDNAs encoding the HBXIP protein, with all clones encoding the full-length protein (see FIG. 7).

Example 3

Cloning of Survivin, HBXIP and HBX and Production of Recombinant Proteins cDNA cloning and plasmid construction. A cDNA encoding human HBXIP was generated by reverse transcription from Jurkat T cell mRNA using SuperScript II (Gibco, Rockville, Md.), followed by the amplification using the Expand High Fidelity PCR system (Roche, Mannheim, Germany) and oligonucleotide primers as follows: 5'-GACGAAT-TCATGGAGGCGACCTTGGAGCA-3' (forward) (SEQ ID NO: 5) and 5'-GATCTCGAGTCAAGAGGCCATTTGT- GCA-3' (reverse) (SEQ ID NO: 6). The resultant cDNA fragments were ligated into the plasmid pcDNA3-FLAG for mammalian expression (Matsuzawa, S. & Reed, J. C. 2001 *Mol Cell* 7:915-926), or into pET21d-N-His$_6$ and pGEX4T-1 for expression in bacteria. Various fragments of Survivin cDNA were also PCR-amplified from pcDNA3-Survivin (Tamm, I. et al. 1998 *Cancer Res* 58:5315-5320), and subcloned into pcDNA3 (Invitrogen, Carlsbad, Calif.). The gene encoding HBX was synthesized by PCR from DNA obtained from patients with hepatocellular carcinoma, as described previously (Marusawa, H. et al. 2000 *Hepatology* 31:488-495).

Production of recombinant proteins and in vitro protein binding assays. Recombinant proteins were purified essentially as described (Deveraux, Q. L, & Reed, J. C. 1999 *Genes Dev* 13:239-252; Zou, H. et al. 1999 *J Biol Chem* 274:11549-11556). His$_6$-HBX protein was made using the Rapid Translation System (Roche), and 2 µl of synthesized reaction mixture was used for Caspase assays. Purified GST-fusion protein or His$_6$-tagged proteins immobilized on glutathione-Sepharose beads or nickel beads, respectively, were incubated in 1% Triton-X 100/PBS for 1 h at 4° C. Then, the beads were washed with binding buffer (5 mM MgCl$_2$, 10% glycerol, 0.5 mg/ml BSA, 5 mM 2-mercaptoethanol and 50 mM Tris-Cl, pH 7.5) and incubated overnight at 4° C. with various recombinant proteins or in vitro translated-$^{35}$S-labeled proteins produced using TNT-coupled reticulocyte lysates (Promega, Madison, Wis.). Protein on beads were washed four times in binding buffer, and bound proteins were eluted in SDS sample buffer, and subjected to SDS-PAGE, as described previously (Deveraux, Q. L. & Reed, J. C. 1999 *Genes Dev* 13:239-252).

Example 4

Analysis of the Binding of Survivin by HBXIP

HBXIP is a 91 amino-acid protein widely expressed in human tissues, whose function is presently unknown (Melegari, M. et al. 1998 *J Virol* 72:1737-1743). The in vitro binding experiments were performed, in which either purified recombinant Survivin (untagged), which had been produced in bacteria as a Glutathione S-Transferase (GST) fusion protein and then digested by thrombin to release Survivin, or GST-XIAP was incubated with His$_6$-HBXIP, His$_6$-TRAF3 or SMAC-His$_6$ immobilized on nickel beads. Bound proteins were analyzed by immunoblotting using anti-Survivin (upper panel) or anti-XIAP (middle panel) antisera. His$_6$-tagged-proteins were also analyzed by SDS-PAGE/immunoblotting using anti-His$_6$ antibody (lower panel). These experiments confirmed the direct association of Survivin and HBXIP.

Gel-filtration chromatography. Recombinant pro-Caspase-9 (2 µg) was incubated in the presence or absence of 5 µg Survivin and 5 µg HBXIP at 30° C. for 30 min in 20 µl of buffer A. Then, 2 µg purified Apaf1, 200 µM dATP, and 600 nM Cytochrome C was added to total volume of 55 µl. After incubation at 30° C. for 30 min, proteins were size-fractionated through a Superdex-200 column (Amersham Biosciences, Piscataway, N.J.), collecting 100 µl fractions, and 20 µl of each fraction was subjected to SDS-PAGE, then blotted with anti-HBXIP, anti-Survivin, anti-Apaf1, and anti-Caspase-9 antibodies. Alternatively, fractions were incubated with GST-HBXIP, and proteins were recovered on glutathione-Sepharose.

Figure 2:
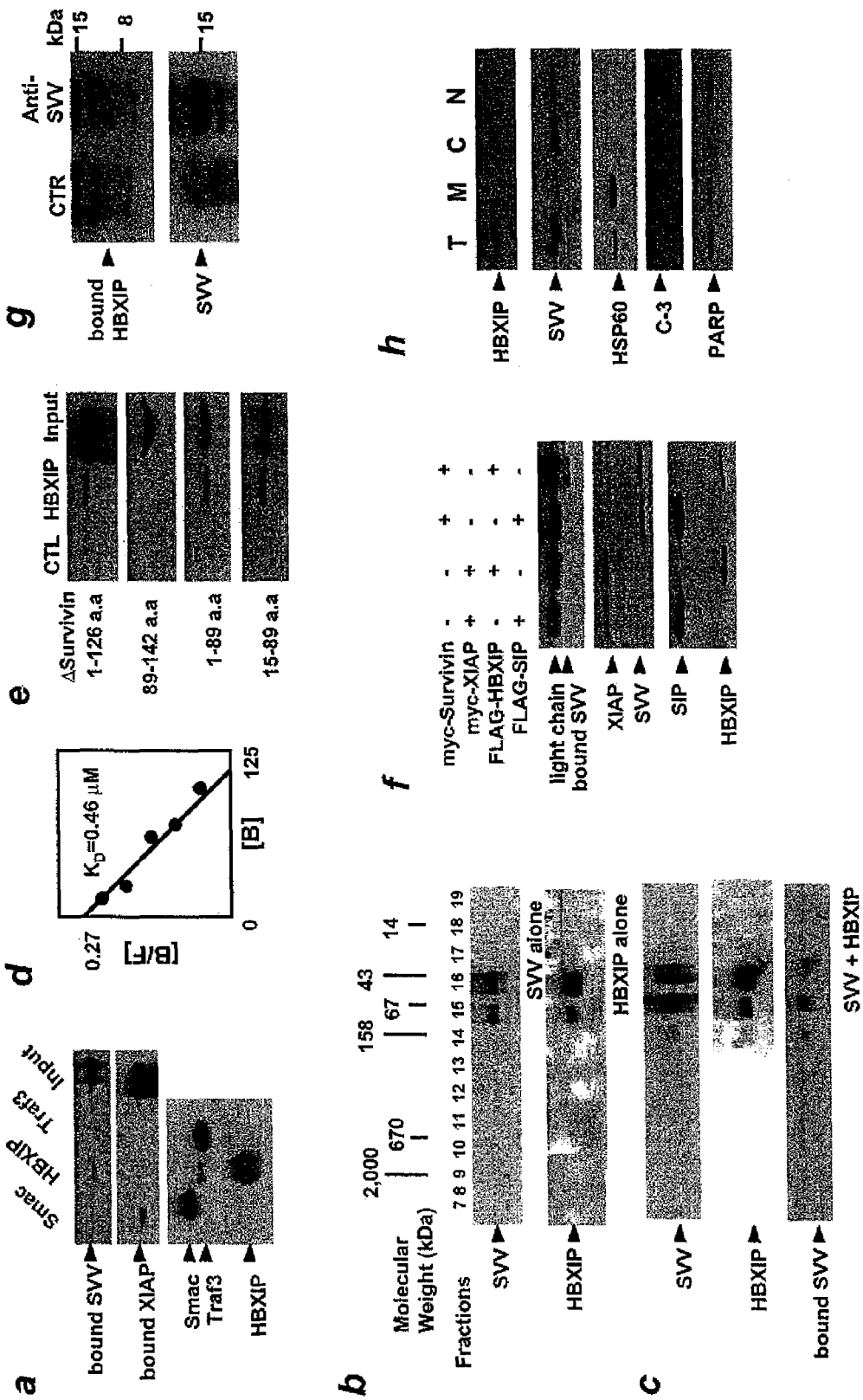
FIG. 2(*a-h*) illustrates that HBXIP directly binds Survivin.

To confirm that Survivin and HBXIP form stable complexes, gel-chromatography experiments were performed in which recombinant purified Survivin, His-HBXIP, or the combination of these proteins was analyzed (FIGS. 2*b* and 2*c*). Purified Survivin alone (FIG. 2*b*, upper panel), His$_6$-HBXIP alone (FIG. 2*b*, lower panel) or a combination of Survivin and His$_6$-HBXIP (FIG. 2*c*) was subjected to gel-filtration chromatography and eluted fractions were analyzed by SDS/PAGE/immunoblotting using anti-Survivin or anti-HBXIP polyclonal antibodies. Additionally, Ni-resin was added to fractions collected in (FIG. 2*c*) to recover His$_6$-HBXIP, and associated Survivin was detected by immunoblotting ("bound Survivin") (FIG. 2*c*, lower panel).

By itself, Survivin eluted at a size roughly consistent with the known dimeric form of this protein. His$_6$-HBXIP, by itself, eluted at a size corresponding roughly to a trimer. When combined, however, some of the Survivin and HBXIP was shifted to higher molecular weight fractions (FIG. 2*c*). Moreover, recovering His$_6$-HBXIP from these slower-eluting fractions using nickel-Sepharose demonstrated the presence of associated Survivin. Thus, HBXIP and Survivin directly bind, forming complexes.

Scatchard analysis showed that HBXIP binds Survivin with sub-micromolar affinity ($K_D$~460 nM) (FIG. 2*d*), which supports the idea that this interaction is sufficiently tight to be physiologically relevant.

To map the region of Survivin required for interaction with HBXIP, a series of fragments of Survivin were prepared by in vitro-translation in the presence of $^{35}$S-L-methionine, and assayed for their ability to bind purified GST-HBXIP. Survivin fragments were incubated with GST-CD40 (cytosolic domain) control protein or GST-HBXIP immobilized on glutathione-Sepharose. Bound proteins were analyzed by autoradiography. Survivin is the smallest of the mammalian IAPs, containing only a single BIR (residues 15-88), followed by a dimerization domain (residues 89-126), and an α-helical region (residues 126-142) that mediates association of this protein with mitotic structures in dividing cells (Verdecia, M. A. et al. 2000 *Nature Struct Biol* 7:602-608). Fragments of Survivin retaining the BIR domain bound HBXIP in vitro, while fragments lacking the BIR did not (FIG. 2*e*). Moreover, a fragment of Survivin representing only the BIR domain bound HBXIP, demonstrating that the BIR of Survivin is necessary and sufficient for HBXIP binding in vitro.

Example 5

Confirmation of Survivin Binding to HBXIP by Co-Immunoprecipitation

For co-immunoprecipitation and immunodepletion assays, cells were cultured with 20 µM MG-132 (Calbiochem) for 8 h before lysing in IP buffer (0.5% NP-40, 1 mM EDTA, 135 mM NaCl and 20 mM Tris-Cl, pH 7.5) containing protease inhibitors (Complete, Roche), and then incubated with primary antibody immobilized on recombinant protein G-Sepharose 4B (Zymed, South San Francisco, Calif.) at 4° C. overnight with constant rotation. Immunoprecipitates were washed with IP buffer four times and suspend in SDS sample buffer, then boiled and analyzed by SDS-PAGE/immunoblotting. Immunodepletion analysis was performed as described using 5 µl of anti-Survivin antiserum or preimmune serum conjugated with 20 µl of protein A-Sepharose (Pathan, N. et al. 2001 *J Biol Chem* 276:32220-32229).

HBXIP binding to Survivin in cells was confirmed by co-immunoprecipitation assays, using epitope-tagged proteins produced in HEK293T cells by transient transfection (FIG. 2*f*). 293T cells were transiently transfected with plasmids encoding myc-tagged Survivin or myc-XIAP, together with FLAG-HBXIP or FLAG-SIP (control). Lysates were subjected to immunoprecipitation using anti-FLAG epitope antibody. Immunoprecipitates were analyzed by immunoblotting using anti-myc antibody (upper panel). Lysates were also blotted by anti-myc (middle panel) or anti-FLAG antibodies (lower panel). Moreover, HBXIP bound to Survivin but not to XIAP, confirming a specific interaction. Binding of endogenous HBXIP to endogenous Survivin was also detected by co-immunoprecipitation assays, using anti-Survivin antibody to immunoprecipitate Survivin, followed by immunoblot analysis of the resulting immune-complexes using anti-HBXIP antiserum. In this experiment lysates from untransfected HepG2 cells were prepared for immunoprecipitation with anti-Survivin antisera, followed by blotting with anti-HBXIP or anti-Survivin antibodies. (FIG. 2g).

Example 6

Antibodies Specific to Survivin, HBXIP, Pro-Caspase-9, Pro-Caspase-3, and XIAP

Polyclonal antisera specific for HBXIP were generated in rabbits using purified recombinant $His_6$-HBXIP as an immunogen. Rabbit polyclonal antibody against pro-Caspase-9, pro-Caspase-3, XIAP and Survivin have been described (Krajewski, S. et al. 1999 *PNAS USA* 96:5752-5757; Tamm, I. et al. 1998 *Cancer Res* 58:5315-5320; Krajewska, M. et al. 1997 *Cancer Res* 57:1605-1613). Rabbit polyclonal antibody recognizing human Apaf1 was purchased from Cayman Chemical Company (Ann Arbor, Mich.). Mouse monoclonal antibodies against active Caspase-9 and Cytochrome C were purchased from Pharmingen (San Diego, Calif.). Rabbit polyclonal anti-HBX antibody was generously provided by Robert J. Schneider (New York University Medical School).

Example 7

Subcellular Localization of Survivin and HBXIP

Subcellular fractionation experiments were performed to determine whether Survivin and HBXIP reside in the same cellular compartment in vivo. Cells were lysed in hypotonic buffer (10 mM Tris-HCl pH 7.5, 10 mM NaCl, 1 mM EDTA, protease inhibitors Complete, Roche) and centrifuged at 700 g for 5 min to obtain nuclear pellets. The resulting supernatants were further centrifuged at 100,000 g for 60 min to obtain membranes (pellet) and soluble cytosolic (supernatant) fractions. Lysates from unfractionated 293 cells (T) and from subcellular fractions (M; membrane, C; cytoplasmic, N; nuclear), normalized for cell-equivalents, were analyzed by immunoblotting using anti-HBXIP and anti-Survivin. Blotting using anti-HSP60, anti-Caspase-3 and anti-PARP antibodies was also performed as markers for membrane (mitochondrial), cytosolic, and nuclear proteins, respectively (FIG. 2h).

Both HBXIP and Survivin were found predominantly in the cytosolic fraction, though some Survivin was also seen in the nuclear fraction (FIG. 2h).

Example 8

HBXIP Collaborates with Survivin in Suppressing Caspase-9 Activation

Figure 3:
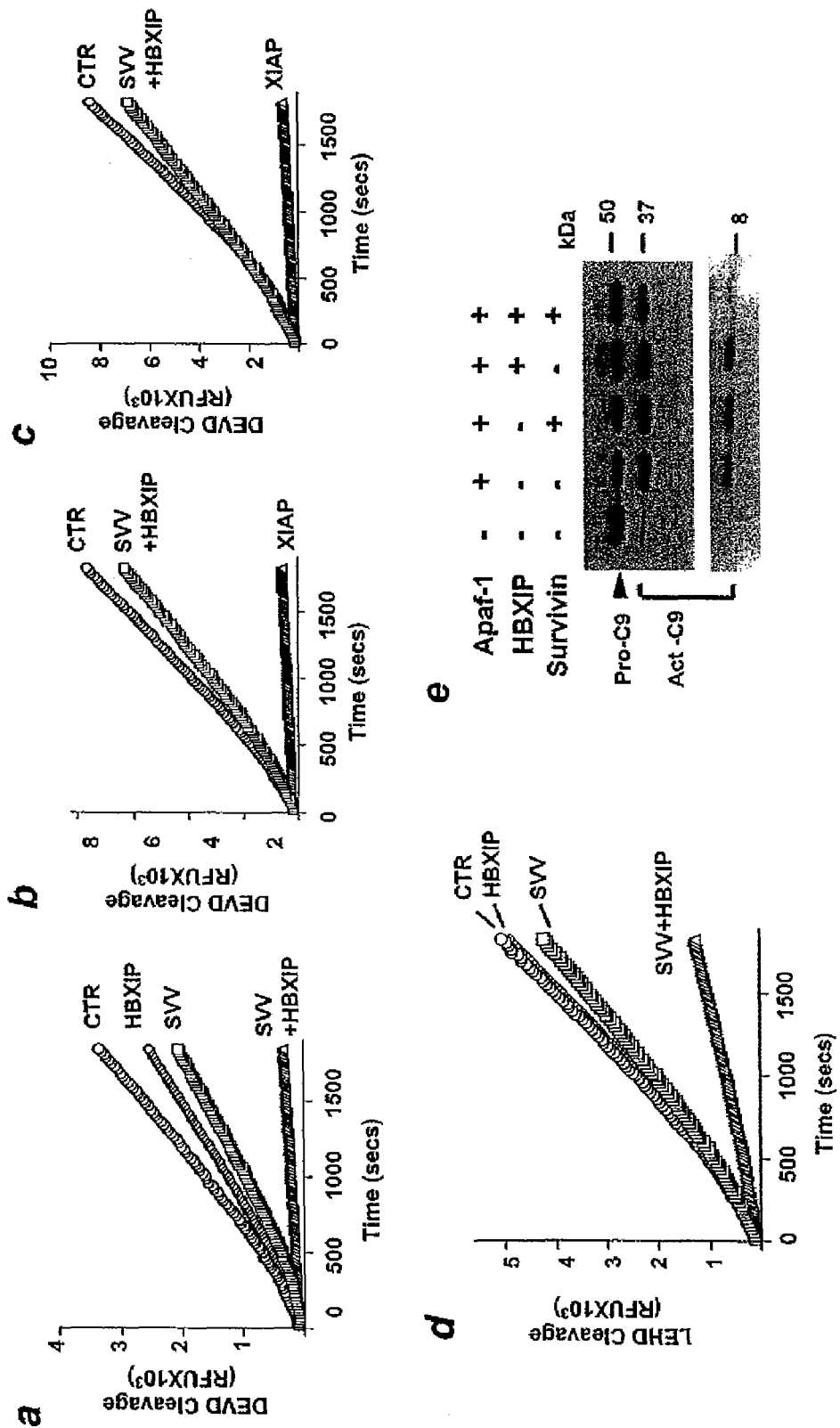
FIG. 3(*a-e*) shows that HBXIP collaborates with Survivin to suppress Caspase-9 activation.

To explore the functional significance of the interaction of HBXIP with Survivin, the effects of recombinant HBXIP alone and in combination with Survivin on activation of Caspases in cell lysates stimulated with Cytochrome C were evaluated. At concentrations below 200 nM, addition of either HBXIP or Survivin individually to cell lysates only slightly suppressed the generation of Caspase protease activity, as measured by the hydrolysis of Ac-DEVD-AFC (FIG. 3a). In contrast, the combination of HBXIP and Survivin nearly completely suppressed Cytochrome C-mediated activation of Caspases, implying functional synergy of these proteins. However, if Survivin and HBXIP were added after Cytochrome C stimulation, Caspase-activity was not suppressed, implying that these proteins block the activation event but do not suppress Caspases once they have been activated. Replacing either Survivin or HBXIP with various control proteins (e.g., GST; GST-CD40; $His_6$-TRAF3) failed to suppress Caspase activity, confirming the specificity of these results.

In contrast to Cytochrome C, addition of the combination of Survivin and HBXIP to cell lysates did not significantly inhibit Caspase activation induced by addition of either purified recombinant active Caspase-8 (FIG. 3b) or Granzyme B (FIG. 3c). By comparison, XIAP completely suppressed effector Caspase activity in these lysates. These findings therefore show that Survivin selectively inhibits Caspase activation via the Cytochrome C pathway, whereas XIAP has broader activity.

The ability of the combination of HBXIP and Survivin to selectively suppress Caspase activation induced by Cytochrome C prompted further exploration into the effects of these proteins on Apaf1-mediated activation of pro-Caspase-9, the apical protease in the Cytochrome C pathway for apoptosis (Li, P. et al. 1997 *Cell* 91:479-489). For these experiments, recombinant Apaf1 and pro-Caspase were produced in and purified from insect cells, as described (Zou, H. et al. 1999 *J Biol Chem* 274:11549-11556). After addition of Cytochrome C and dATP to induce Apaf1 oligomerization, Caspase-9 activity was measured by cleavage of the fluorigenic substrate Ac-LEHD-AFC (FIG. 3d) and pro-Caspase-9 processing was monitored by immunoblotting (FIG. 3e). Addition of either recombinant purified Survivin or HBXIP individually was ineffective at blocking Apaf1-mediated activation and proteolytic processing of pro-Caspase-9 in vitro. In contrast, the combination of Survivin and HBXIP effectively suppressed generation of Caspase-9 protease activity (FIG. 3d), and also reduced proteolytic processing of 50 kDa pro-Caspase-9 into 35 kDa large and ~12 kDa small subunits typical of the active protease (FIG. 3e). This effect of combining HBXIP and Survivin was not merely due to the presence of more protein in the reactions, because substituting various control proteins for either HBXIP or Survivin (e.g. GST; GST-CD40; $His_6$-TRAF3) failed to inhibit Apaf1-mediated activation of pro-Caspase-9.

Example 9

HBXIP/Survivin Complexes can Bind Pro-Caspase-9, Preventing its Activation by Apaf1

Figure 4:
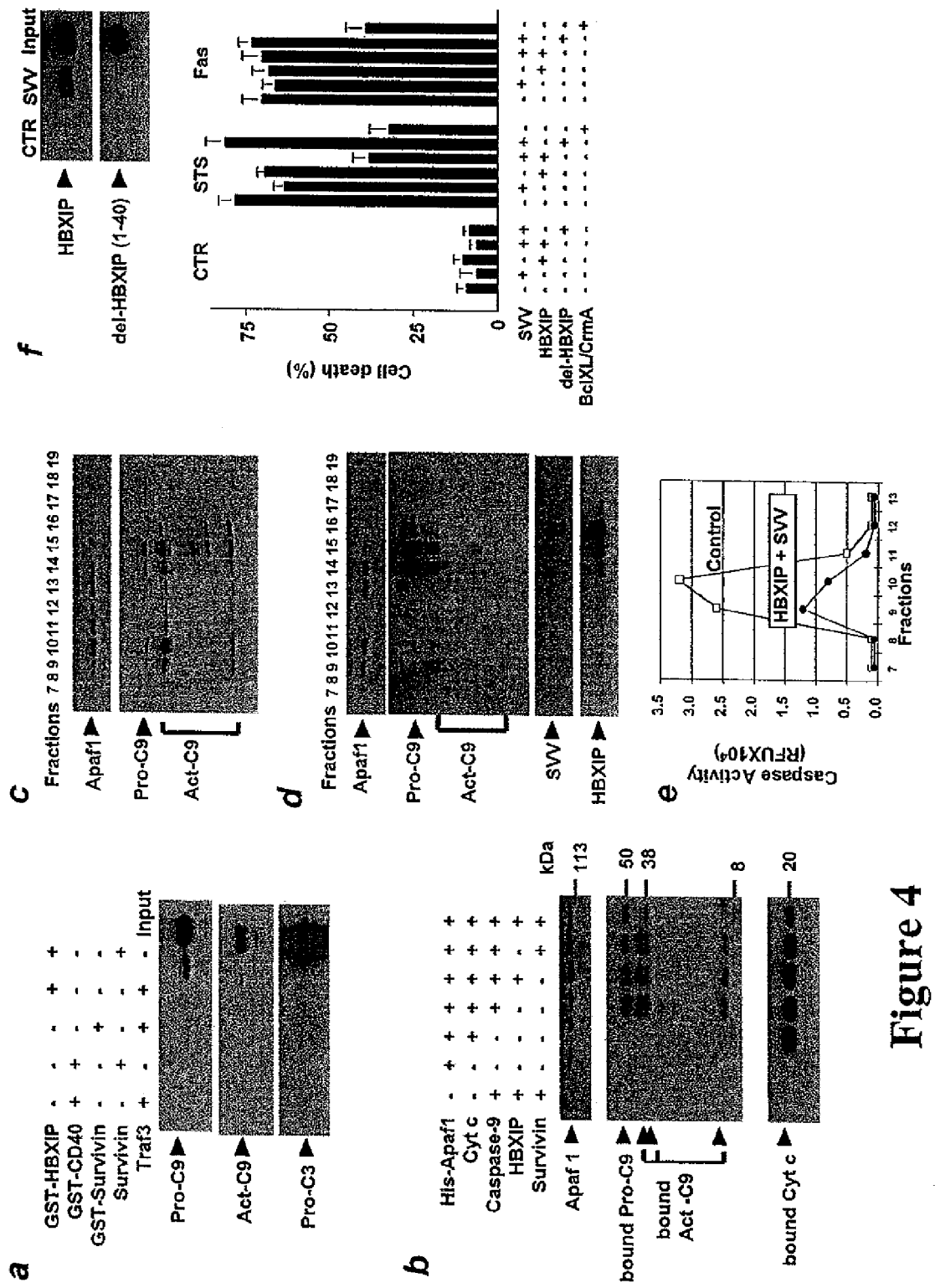
FIG. 4(*a-f*) shows that the combination of HBXIP and Survivin inhibits the recruitment of pro-Caspase-9 to activated Apaf1.

To explore the mechanism by which the combination of Survivin and HBXIP suppresses pro-Caspase-9 activation, testing was performed to determine whether these proteins can bind pro-Caspase-9 in vitro. For these experiments, GST-Survivin, GST-CD40 or GST-HBXIP with or without purified Survivin (untagged) was incubated with $His_6$-pro-Caspase-9, and the HBXIP bound proteins were analyzed by immunoblotting using an anti-Caspase-9 antiserum (Krajewski, S. et al. 1999 *PNAS USA* 96:5752-5757). For comparative purposes, similar experiments were also performed using recombinant purified active $His_6$-Caspase-9 (lacking CARD domain) (Stennicke, H. R. et al. 1997 *J Biol Chem* 274:8359-8362) and His$_6$-pro-Caspase-3 (Stennicke, H. R. & Salvesen, G. S. 1997 *J Biol Chem* 272:25719-25723). GST-fusion proteins were recovered using glutathione-Sepharose and bound proteins were detected by immunoblotting using anti-Caspase-9 or anti-Caspase-3 antisera. An equivalent amount of proteins was loaded directly in gels as a control ("input"). In the absence of Survivin, GST-HBXIP failed to "pull-down" Caspases (FIG. 4a). However, when Survivin was included, then pro-Caspase-9 was pulled-down with GST-HBXIP, but not with control GST-CD40 protein. GST-HBXIP also pulled-down active Caspase-9, in the presence but not the absence of Survivin, but the proportion of active Caspase-9 that associated with GST-HBXIP under these conditions was far less than pro-Caspase-9. No association with Caspase-3 was found. Also, when Survivin was used alone (as a GST-fusion protein) for pull-down assays, no binding to Caspases was detected (FIG. 4a, lane 3), providing further evidence that Survivin cannot bind Caspases by itself. Taken together with the data on Caspase-9 activity, it was shown that HBXIP/Survivin complexes can bind pro-Caspase-9, preventing its activation by Apaf1.

Given that HBXIP/Survivin complexes bind pro-Caspase-9, further analysis was performed to assess whether these proteins interfere with association of pro-Caspase-9 with active Apaf1. For these experiments, recombinant purified His$_6$-Apaf1 was incubated with $^{35}$S-labeled pro-Caspase-9 (produced by in vitro translation), Cytochrome C and dATP, in the presence or absence of Survivin, HBXIP, or the combination of these proteins. Then, His$_6$-Apaf1 was recovered on Ni-chelation resin, and associated proteins were analyzed by autoradiography (Caspase-9) (FIG. 4b) or by immunoblotting using anti-Cytochrome C antibody (FIG. 4c, FIG. 4d). In the absence of Survivin and HBXIP, full-length ~50 kDa pro-Caspase-9 as well as the 35-37 kDa large and 12 kDa small subunits of processed Caspase-9 were recovered with His$_6$-Apaf1 on Ni-resin (FIG. 4b). In contrast, when pro-Caspase-9 was pre-incubated with the combination of HBXIP and Survivin before the introduction of His$_6$-Apaf1, the amount of Pro-Caspase and processed Caspase-9 recovered with His$_6$-Apaf1 on Ni-resin was significantly reduced, indicating that HBXIP-Survivin complexes prevented recruitment of pro-Caspase-9 to Cytochrome C-activated Apaf1 (FIG. 4b). When various control proteins were substituted for either Survivin or HBXIP, then pro-Caspase-9 association with Apaf1 was not blocked. Also, Survivin/HBXIP complexes did not interfere with binding of Cytochrome C to Apaf1 (FIG. 4b), demonstrating a specific effect on recruitment of pro-Caspase-9.

Example 10

Survivin/HBXIP Inhibits Apoptosome Formation and Activity

The multiprotein complex containing Apaf1, Cytochrome C, and Caspase-9 is called the "apoptosome" (Zou, H. et al. 1999 *J Biol Chem* 274:11549-11556). Assays of apoptosome activity were conducted essentially as described, using proteins produced in and purified from baculovirus-infected insect cells (Zou, H. et al. 1999 *J Biol Chem* 274:11549-11556). Recombinant pro-Caspase-9 (4 nM) was incubated with purified Survivin (40 nM), HBXIP (40 nM), the combination of these proteins, or equivalent amounts of various control proteins such as CD40 or TRAF3 at 30° C. for 10 min. Then, 4 nM recombinant Apaf1 was added, followed by 200 µM dATP, 600 nM Cytochrome C, and 10 µM of recombinant pro-Caspase-3 in a total of 40 µl of buffer A, as described above. After incubation, 160 l of Caspase buffer containing Ac-DEVD-AFC (100 µM final concentration) was added. Alternatively, for measurements of Caspase-9 activity, 200 nM of pro-Caspase-9 was incubated with 100 nM of Apaf1 with 2 µM of various control or specific recombinant proteins under the same conditions, then Ac-Leu-Glu-His-Asp-AFC (Ac-LEHD-AFC, Calbiochem) fluorigenic substrate was added.

To further address the mechanism by which Survivin/HBXIP complexes inhibit Apaf1-induced activation of pro-Caspase-9, apoptosome complexes were subjected to gel-filtration chromatography, analyzing column fractions by SDS-PAGE/immunoblotting using antibodies recognizing Apaf1 or Caspase-9 (FIG. 4c). In the absence of Survivin and HBXIP, two peaks of Apaf1 were detected, and Caspase-9 co-eluted with the larger or these complexes (FIG. 4c), consistent with prior reports (Zou, H. et al. 1999 *J Biol Chem* 274:11549-11556). In contrast, when apoptosome assembly was induced in the presence of Survivin and HBXIP, and then gel-filtration chromatography analysis was performed, very little Caspase-9 co-eluted with Apaf1. Also, more of the Caspase-9 was present in the pro-enzyme form (~50-kDa as opposed to ~35 kDa) when HBXIP and Survivin were included. Moreover, the column fractions in which the majority of the pro-Caspase-9 eluted also contained Survivin and HBXIP (FIG. 4d).

In addition, column fractions were monitored for Caspase-9 activity, using an assay in which the Caspase-9 substrate, pro-Caspase-3, was added and then Caspase-3 activity was measured by AC-DEVD-AFC hydrolysis. Comparisons of apoptosome-associated Caspase-9 activity demonstrated markedly reduced Caspase-9 activity when Survivin and HBXIP were included (FIG. 4e). It is therefore concluded that the combination of HBXIP and Survivin reduces pro-Caspase-9 activation by interfering with apoptosome assembly.

If Survivin and HBXIP prevent pro-Caspase-9 activation by Apaf1, then one would predict that co-expressing Survivin and HBXIP in cells would provide protection from apoptotic stimuli that operate through a Caspase-9-dependent pathway, but not from stimuli that induce apoptosis through other routes. Compared were the effects of transfecting plasmids encoding Survivin, HBXIP, or the combination of these proteins on apoptosis induced by Staurosporine and anti-Fas antibody, stimuli that operate through Caspase-9-dependent and -independent pathways, respectively (Salvesen, G. S. 2002 *Cell Death Differ* 9:3-5).

Cell lines were cultured in DMEM with 10% fetal calf serum, 1 mM L-glutamine, and antibiotics. Cells were transfected with various plasmids in combination with pEGFP (Clontech) using Fugene-6 transfection reagent (Roche). After culturing 1.5 days, apoptosis was induced by anti-Fas monoclonal antibody CH-11 (500 ng/ml; MBL, Nagoya, Japan), or Staurosporine (100 nM). Both floating and attached cells were collected 24 h after apoptosis induction, and analyzed by 1 µg/ml of 4',6-diamidino-2'-phenylindole dihydrochloride (DAPI) staining for assessing nuclear morphology. The percentage of apoptotic cells revealed by DAPI staining was determined by fluorescence microscopy, counting a minimum of 200 GFP-positive cells.

In addition, wild-type HBXIP was compared with a mutant containing only the first 40 amino-acids of HBXIP protein, del-HBXIP (1-40), that we empirically determined is incapable of binding Survivin (FIG. 4f upper panel). At the plasmid concentrations used, either Survivin or HBXIP only slightly suppressed apoptosis in transfected HT1080 cells (FIG. 4f, lower panel). In comparison, Bcl-XL, which inhibits Cytochrome C release from mitochondria (Yang, J. et al. 1997 *Science* 275:1129-1132) and CrmA, which inhibits Caspase-8 (Zhou, Q. et al. 1997 *J Biol Chem* 272:7797-7800) suppressed apoptosis induced by Staurosporine and anti-Fas antibody, respectively, serving as positive-controls for these assays. However, when Survivin and HBXIP were co-expressed in HT1080 cells, then apoptosis induced by Staurosporine, but not Fas, was suppressed (FIG. 4f). Immunoblot analysis of transfected cells, which were treated with a broad-spectrum Caspase inhibitor (zVAD-fmk) to prevent apoptosis, confirmed production of all proteins and demonstrated comparable levels of HBXIP and del-HBXIP (1-40).

Taken together, these data demonstrate a collaborative role of Survivin and HBXIP in selectively suppressing the Caspase-9-dependent pathway for apoptosis, consistent with the idea that these proteins interfere with pro-Caspase-9 activation.

Example 11

Endogenous HBXIP and Survivin Regulate Caspase Activation in Cancer Cells

Figure 5:
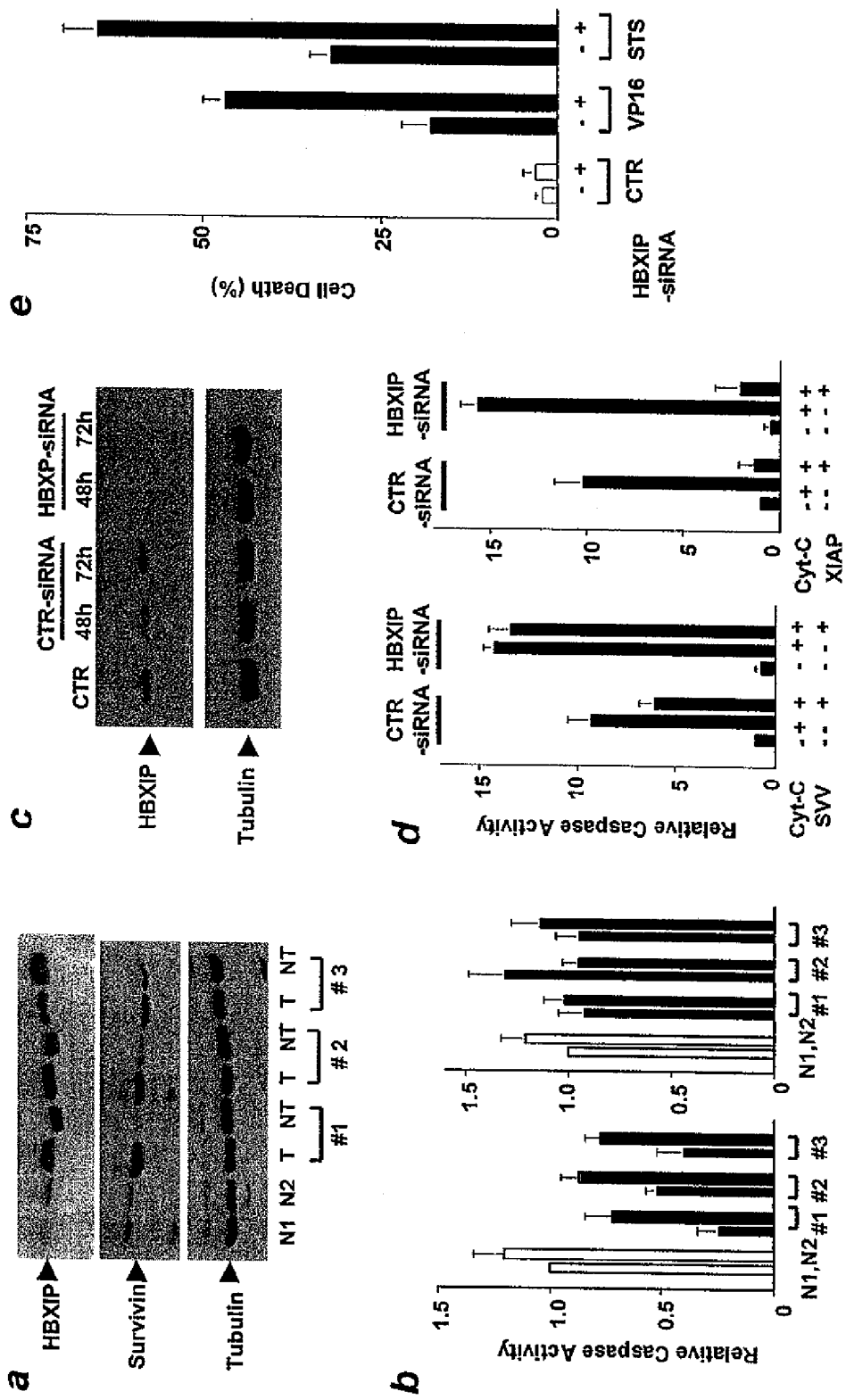
FIG. 5(*a-e*) shows regulation of Caspase activation and apoptosis by endogenous HBXIP.

To explore the role of HBXIP in the pathogenesis of human liver disease associated with HBV infection, the expression of this protein was first analyzed by immunoblotting in primary hepatocellular carcinoma tissues, as well as non-cancerous regions of the same livers of patients with chronic HBV infection. The non-cancerous regions of these liver tissues included two cases with liver cirrhosis (Case #1 and 2) and one with chronic hepatitis (Case #3). As a control for non-HBV infection, normal regions of hepatic tissue from patients with metastatic colon cancer were also examined. Levels of HBXIP protein were elevated in both cancerous and non-cancerous liver tissue of patients with chronic HBV infection, compared to hepatic tissue of patients without a history of HBV infection (FIG. 5a). Based on normalization to α-tubulin levels, HBXIP levels were determined to be 2- to 7-fold higher in the tissues of patients with chronic HBV infection compared to non-infected liver, based on scanning-densitometry analysis of immunoblots. Interestingly, probing the same blots with anti-Survivin antibody revealed higher levels of Survivin protein in tumor tissue compared non-cancerous regions of the same livers in all 3 specimens examined (FIG. 5a).

Since the combination of Survivin and HBXIP interferes with Cytochrome C-mediated activation of pro-Caspase-9 (see above), it was determined whether a correlation exists between elevated expression of these proteins in HBV-associated hepatocellular carcinomas and resistance to Cytochrome C-induced Caspase activation. Accordingly, lysates from the liver tissues were normalized for total protein content, and then incubated with Cytochrome C and dATP to induce Apaf1-mediated activation of Caspases. Compared to non-infected liver tissue, Cytochrome C-inducible Caspase activity was significantly reduced in lysates of both cancerous (p<0.01) and non-cancerous (p<0.01) liver tissue derived from patients with chronic HBV infection (FIG. 5b, left panel), with induction of DEVD-cleaving Caspase activity more depressed in cancerous tissues than non-cancerous tissues from HBV-infected individuals (p<0.01). In contrast, no significant difference in Caspase activity induced by exogenously added Granzyme B was found, comparing normal, HBV-infected, and cancer tissues (FIG. 5b, right panel). Thus, HBV-associated elevations in expression of HBXIP correlate with selective resistance to Cytochrome c-mediated activation of Caspases in extracts from primary patient tissues.

Example 12

Reduction of HBXIP Expression by siRNA Relieves Survivin-Mediated Suppression of Apoptosis To determine whether HBXIP is necessary for the inhibitory effect of Survivin, small-interfering RNA (siRNA) were used to reduce expression of endogenous HBXIP in HeLa cells. siRNA duplexes composed of 21-nucleotide sense and antisense strands were synthesized by Dharmacon Research (Lafayette, Colo.). RNA oligonucleotides used for targeting HBXIP in this study were: HBXIP-S1,5'-GCAGCUAAGC-UAACCUCUGTT-3' (sense) (SEQ ID NO: 7), and HBXIP-AS1 5'-TTCGUCGAUUCGAUUGGAGAC-3' (antisense) (SEQ ID NO: 8). HeLa cells were plated in 6 cm wells at $2.5 \times 10^5$ cells per well 24 h before transfection. 20 µM siRNA in 25ll of Oligofectamine reagent (Invitrogen) was incubated in serum-free Opti-MEM medium for 20 min, then the transfection mixture was added to cells, incubated at 37° C. for 4 h, followed by addition of fresh medium containing serum. At 36 hours after transfection, cells were analyzed for apoptosis or lysed for immunoblotting.

Transfection of HBXIP-specific but not control double-strand synthetic RNAs reduced levels of endogenous HBXIP protein in HeLa cells, which was sustained for at least 3 days, as determined by immunoblot analysis (FIG. 5c). It was also confirmed that the levels of other proteins required for Cytochrome C responsiveness (Apaf1, pro-Caspase-9, pro-Caspase-3) were not affected by treatment with HBXIP-siRNA. Caspase activity induced by Cytochrome C in cell lysates derived from siRNA-treated cells was then measured. Extracts prepared from HeLa cells after treatment with HBXIP-siRNA or control-RNA were incubated with Cytochrome c and dATP, in the presence or absence recombinant Survivin (left panel) or XIAP (right panel), and Caspase activity was measured based on release of AFC from Ac-DEVD-AFC substrate (mean±SE; n=3 determinations) (FIG. 5d). Cytochrome C (with dATP) was more effective at activating Caspases in cell extracts treated with HBXIP-siRNA compared to control RNA-treated cells, confirming a role for HBXIP as an endogenous antagonist of this Caspase activation pathway. In control extracts, addition of recombinant purified Survivin suppressed Cytochrome C-mediated activation of Caspases. In contrast, Survivin failed to suppress Caspase activation in extracts in which HBXIP expression was knocked-down (FIG. 5d left panel). By comparison, siRNA-mediated knock-down of HBXIP did not affect the inhibitory effect of recombinant XIAP on Cytochrome C-mediated Caspase activation (FIG. 5d right panel), demonstrating the specificity of these results.

Similar conclusions were reached from experiments using intact cells in which endogenous HBXIP expression was knocked-down by siRNA, showing that more apoptosis was induced by agents that trigger Caspase-9-dependent apoptosis, such as DNA-damaging agent VP16 (etoposide) and kinase-inhibitor Staurosporine (STS), when HBXIP levels were reduced (FIG. 5e). In these experiments the percentage of apoptotic cells (mean±SE; n=3) was determined by DAPI-staining following culture of control-RNA- or HBXIP siRNA-transfected HeLa cells with Etoposide (VP-16) or Staurosporine (STS).

Example 13

HBX Protein Collaborates with HBXIP in Suppressing Caspase Activation

The viral oncoprotein HBX is encoded in the HBV genome, and has been implicated in hepatocellular carcinogenesis through uncertain mechanisms (reviewed in Murakami, S. 2001 *J Gastroenterol* 36:651-660). In vitro protein binding assays were performed in which recombinant His$_6$-HBX was incubated with GST-HBXIP, GST-Survivin, or GST-CD40 (control) immobilized on glutathione-Sepharose. Bound proteins were analyzed by immunoblotting using anti-HBX antibody. This confirmed previously reported observations that HBX associates with HBXIP (FIG. 6a). HBX, in contrast, did not bind Survivin.

The ability of HBX to associate with HBXIP raised the question of whether this viral oncogenic protein could effect Caspases. Since attempts to produce soluble recombinant HBX in bacteria failed, in vitro translation using bacterial extracts was used for production of this viral protein. His$_6$-HBX or control [CTR] proteins, purified His$_6$-HBXIP, purified Survivin, or various combinations of these proteins were added to 293 cell extracts normalizing all samples for total protein added using control recombinant proteins, then Cytochrome c and dATP were added, and Caspase activity was measured 30 min later based on hydrolysis of Ac-DEVD-AFC. Release from fluorogenic AFC from AC-DEVD-AFC was measured continuously. Addition of HBX protein to lysates prepared from HepG2 hepatocellular cancer cells suppressed Caspases activation induced by Cytochrome C and dATP, while control proteins prepared in the same manner had little effect (FIG. 6b). In addition, this viral protein augmented the inhibitory effect of recombinant purified HBXIP and Survivin on Cytochrome C-mediated Caspase activation (FIG. 6c), prompting examination into whether HBX protein associates with HBXIP/Survivin complexes.

For this purpose, co-immunoprecipitation assays were carried out using epitope-tagged HBX, HBXIP and Survivin expressed by transient transfection in HEK293T cells. Since HBX does not directly bind Survivin (FIG. 6a), it was reasoned that over-expressing HBXIP would increase the amounts of Survivin immunoprecipitated with HBX by bridging these two proteins together. HEK293 cells were transiently transfected with plasmids encoding FLAG-tagged-HBX or FLAG-SIP (as a control) together with Myc-Survivin or HA-HBXIP or control plasmid. Lysates were subjected to immunoprecipitation using anti-FLAG epitope antibody, demonstrating increased association of Survivin with HBX when HBXIP was co-expressed (compare last two lanes at right). Immunoprecipitates were analyzed by immunoblotting using anti-Survivin antibody (upper panel). Lysates were also analyzed by immunoblotting using anti-HBX (middle panel) or anti-HA antibodies (lower panel), confirming production of the intended proteins. Indeed, when HBX and Survivin were co-expressed with HBXIP, considerably more Survivin was associated with HBX-immunoprecipitates (FIG. 6d). These data therefore are consistent with the idea that HBX, HBXIP, and Survivin form complexes.

To address whether Survivin/HBXIP complexes were still capable of binding pro-Caspase-9 in the presence of HBX, we performed in vitro protein interaction assays, examining the association of pro-Caspase-9 with GST-HBXIP when Survivin, HBX, or both proteins were added. His$_6$-pro-Caspase-9 was incubated with GST-HBXIP(+) or GST-CD40 control protein (−), in the presence or absence of His$_6$-HBX and untagged Survivin. GST-fusion proteins were recovered on glutathione-Sepharose and bound proteins were detected by immunoblotting using anti-Caspase-9, anti-Survivin, or anti-HBX antisera. As shown above, GST-HBXIP pulled-down pro-Caspase-9 when Survivin was included in the binding assays (FIG. 6e lane 3). Addition of HBX did not impair pro-Caspase-9 association with GST-HBXIP, and instead increased pro-Caspase-9 binding slightly (FIG. 6e lane 4). Thus, rather than competing for binding to HBXIP, the HBX protein appears to form complexes with HBXIP in a manner that does not preclude simultaneous association with Survivin and pro-Caspase-9, and which may even enhance formation of multiprotein complexes containing these proteins.

Figure 6:
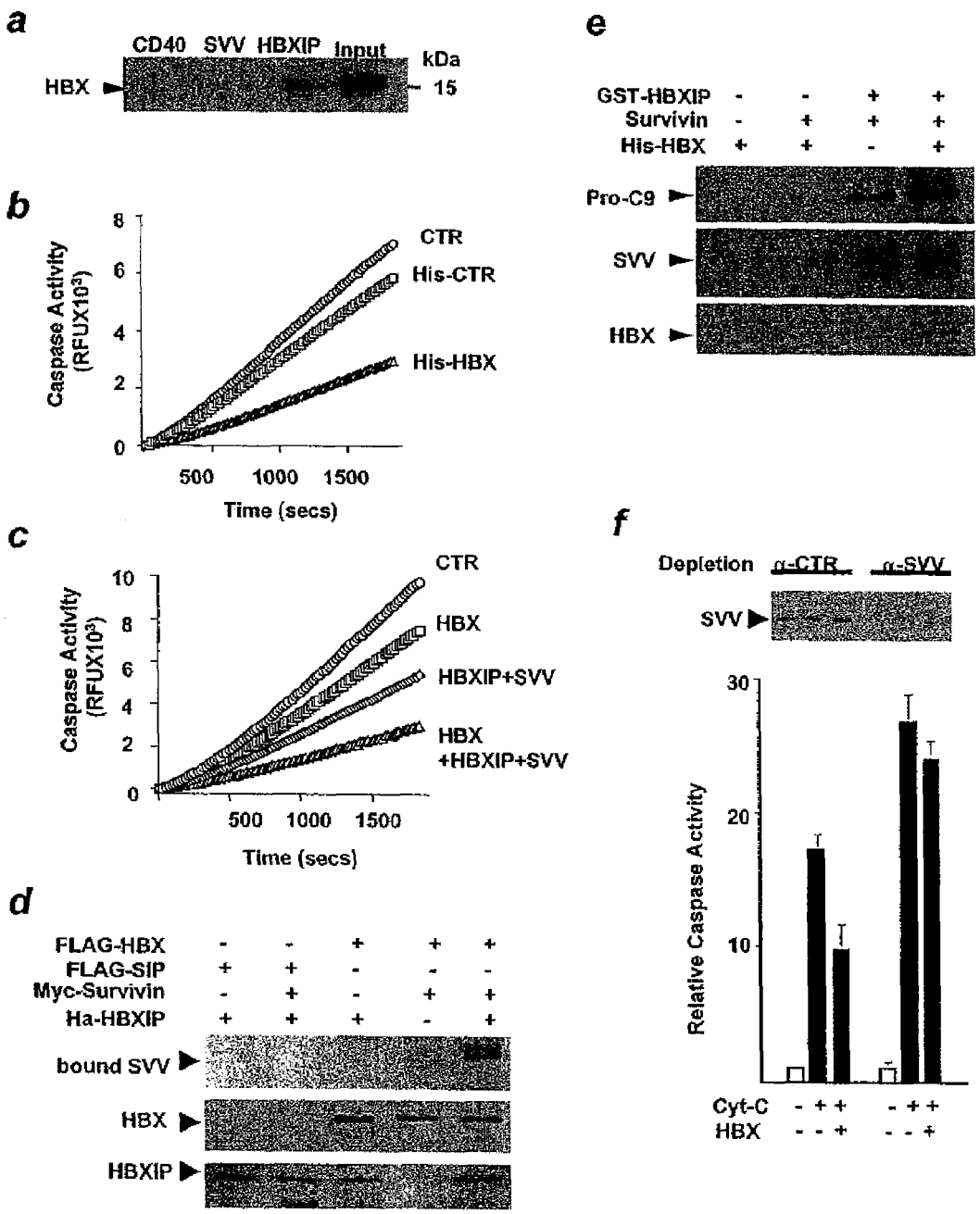
FIG. 6(*a-f*) shows that HBX associates with Survivin through HBXIP and suppresses Caspase activation.

To further explore whether HBX suppresses Caspase activity through a Survivin-dependent mechanism, endogenous Survivin was immunodepleted from HepG2 cell lysates using anti-Survivin antisera or preimmune serum (CTR) and then equivalent amounts analyzed by immunoblotting using anti-Survivin antibody (top panel). Further, equivalent volumes of extracts were analyzed for Caspase activity based on Ac-DEVD-AFC cleavage, where lysates were incubated with recombinant HBX (+) or control protein (−) prior to stimulation with Cytochrome c and dATP. In extracts subjected to mock immunodepletion, HBX suppressed Caspase activation by roughly half (FIG. 6f). In contrast, when Survivin was immunodepleted, it was found that Cytochrome C was more potent at activating Caspases and that HBX had little inhibitory activity (FIG. 6). Thus, HBX fails to inhibit Caspases in the absence of Survivin.

Example 14

Pathways Leading to Cell Survival and Cell Death

In summary, it was discovered that Survivin requires an additional partner protein in its mechanism of Caspase inhibition that results in inhibition of apoptosis. Using yeast two-hybrid screens of cDNA libraries, HBXIP was identified as a candidate Survivin-binding protein, and the association of HBXIP with Survivin was confirmed in vitro and in cells by several methods. Importantly, using purified components, it was found that the combination of Survivin and HBXIP was required for binding and preventing Apaf1-mediated activation of pro-Caspase-9, whereas neither protein individually was adequate. Moreover, the combination of Survivin and HBXIP, but neither alone, reduced recruitment of pro-Caspase-9 to Cytochrome c-activated Apaf1. Consistent with the discovery that Survivin requires HBXIP for its Caspase-inhibitory function, it was shown that Survivin lost its ability both to suppress Cytochrome C-mediated activation of Caspases in cell extracts and to inhibit apoptosis when expressed in intact cells in which endogenous HBXIP had been largely eradicated by siRNA.

HBXIP was originally isolated as a human protein which binds the viral oncogenic protein, HBX, of the Hepatitis 13 Virus (HBV) (Melegari, M. et al. 1998 *J Virol* 72:1737-1743). HBXIP encodes a protein of 9,6-kDa with a putative leucine zipper motif. Expression of HBXIP mRNA has been demonstrated in essentially all tissues examined to date, and is not limited to the liver (Melegari, M. et al. 1998 *J Virol* 72:1737-1743). In the context of HBV-infection, HBXIP reportedly reduces viral replication and abolishes the transactivation function of viral HBX protein (Melegari, M. et al. 1998 *J Virol* 72:1737-1743), however, little is known about the physiological roles of HBXIP in human cells. The cellular HBXIP protein is conserved in mice and rodents, suggesting an evolutionarily conserved function. Based on the data presented here, HBXIP is envisioned to be an anti-apoptotic co-factor of Survivin. Consistent with this idea, siRNA-mediated reductions in endogenous HBXIP levels sensitized cells to apoptosis, while over-expression of HBXIP suppressed apoptosis in collaboration with Survivin.

Up-regulation of HBXIP was found in both cancerous and non-malignant liver tissue of humans with chronic HBV-infection, compared to normal hepatic tissue. In this regard, chronic HBV infection is known to cause pre-neoplastic changes in liver (Lok, A. S. 2000 *J Hepatol* 32:89-97), explaining the observed elevations in HBXIP in both non-malignant and tumor tissue of HBV-diseased livers.

It is estimated that more than 380 million HBV carriers are present worldwide today, with chronic HBV infection representing a major global pathogenic factor for development of hepatocellular carcinoma (Lok, A. S. 2000 *J Hepatol* 32:89-97). A crucial role of HBV in hepatocarcinogenesis is beyond doubt, while the mechanisms by which HBV causes the transformation of hepatocytes remain unclear. The HBV genome consists in a 3.2 kbp circular double-stranded DNA molecule with overlapping open reading frames (ORFs) encoding four viral proteins. Among them is HBX, a 154 amino-acid protein that has no recognizable counterpart in humans or other mammalian species. HBX is essential for replication of woodchuck HBV, and transgenic mice engineered to express HBX have increased incidence of hepatocellular cancer, especially when exposed to chemical carcinogens (Kim, C. M. et al. 1991 *Nature* 351:317-320). Thus, HBX is a candidate transforming gene of HBV. Like many viral oncoproteins, HBX is multifunctional protein. HBX exhibits effects on gene transcription, cell proliferation, and apoptosis, and has multiple putative cellular targets besides HBXIP (reviewed in Murakami, S. 2001 *J Gastroenterol* 36:651-660). The effects of HBX on apoptosis are controversial, with evidence suggestive either of suppression or promotion of apoptosis, depending on the cellular context and stimulus. Among the reported molecular effects of HBX is transcription-independent suppression of Caspases (Gottlob, K. et al. 1998 *J Biol Chem* 273:33347-33353), though many alternative mechanisms have also been proposed (reviewed in Murakami, S. 2001 *J Gastroenterol* 36:651-660). These data demonstrate that HBX can associate indirectly with Survivin, through HBXIP. Moreover, depletion of Survivin from cell extracts abolishes the ability of HBX to suppress Caspase activation in vitro. Thus, HBX modulates apoptosis pathways through interactions with HBXIP/Survivin complexes.

The hepatitis B X-interacting protein (HBXIP) is a target for cancer therapy. The interaction of HBXIP with Survivin can be suppressed in neoplastic cells by downregulating the HBXIP expression using siRNA or antisense. The level of HBXIP in neoplastic cells can be reduced in the presence of HBXIP- or Survivin-specific antibodies. The interaction of HBXIP with Survivin may also be inhibited by the use of specific inhibitors, molecular decoys, or the like.

While the present invention has been described in some detail for purposes of clarity and understanding, one skilled in the art will appreciate that various changes in form and detail can be made without departing from the true scope of the invention. All figures, tables, and appendices, as well as patents, applications, and publications, referred to above, are hereby incorporated by reference in their entireties.

What is claimed is:

1. An isolated nucleic acid molecule that inhibits interaction of Survivin with hepatitis B X-interacting protein (HBXIP), wherein the nucleic acid molecule comprises an antisense nucleic acid molecule or siRNA molecule that inhibits expression of HBXIP, wherein the nucleic acid molecule comprises at least a 15 nucleotide fragment of SEQ ID NO: 7 or complement thereof, but not more than 30 nucleotides.

2. The isolated nucleic acid molecule of claim 1, wherein the nucleic acid molecule comprises a modified backbone.

3. The isolated nucleic acid molecule of claim 2, wherein the modified backbone comprises phosphorothioates.

4. The isolated nucleic acid molecule of claim 1, wherein the nucleic acid molecule has greater than 90% identity with a nucleic acid molecule encoding the HBXIP.

5. The isolated nucleic acid molecule of claim 4, wherein the HBXIP is encoded by the nucleic acid sequence of SEQ ID NO: 3.

6. The isolated nucleic acid molecule of claim 1, wherein the nucleic acid molecule comprises an antisense molecule.

7. The isolated nucleic acid molecule of claim 1, wherein the nucleic acid molecule comprises an siRNA molecule.

8. The isolated nucleic acid molecule of claim 1, wherein the nucleic acid molecule comprises one or more substituted sugar moieties.

9. A pharmaceutical composition comprising:
a) a nucleic acid molecule that inhibits interaction of Survivin with hepatitis B X-interacting protein (HBXIP), wherein the nucleic acid molecule comprises an antisense nucleic acid molecule or siRNA molecule that inhibits expression of HBXIP, wherein the nucleic acid molecule comprises at least a 15 nucleotide fragment of SEQ ID NO: 7 or complement thereof, but is not more than 30 nucleotides; and
b) a pharmaceutically acceptable carrier.

10. The pharmaceutical composition of claim 9, wherein the nucleic acid molecule comprises a modified backbone.

11. The pharmaceutical composition of claim 10, wherein the modified backbone comprises phosphorothioates.

12. The pharmaceutical composition of claim 9, wherein the nucleic acid molecule has greater than 90% identity with a nucleic acid molecule encoding the HBXIP.

13. The pharmaceutical composition of claim 12, wherein the HBXIP is encoded by the nucleic acid sequence of SEQ ID NO: 3.

14. The pharmaceutical composition of claim 9, wherein the nucleic acid molecule comprises an antisense molecule.

15. The pharmaceutical composition of claim 9, wherein the nucleic acid molecule comprises an siRNA molecule.

16. The pharmaceutical composition of claim 9, wherein the nucleic acid molecule comprises one or more substituted sugar moieties.

17. The pharmaceutical composition of claim 15, wherein the siRNA molecule comprises a sense strand encoded by a nucleic acid sequence as shown in SEQ ID NO: 7.

18. The pharmaceutical composition of claim 15, wherein the siRNA molecule comprises an antisense strand encoded by a nucleic acid sequence as shown in SEQ ID NO: 8.

19. The isolated nucleic acid molecule of claim 7, wherein the siRNA molecule comprises a sense strand encoded by a nucleic acid sequence as shown in SEQ ID NO: 7.

20. The isolated nucleic acid molecule of claim 7, wherein the siRNA molecule comprises an antisense strand encoded by a nucleic acid sequence as shown in SEQ ID NO: 8.

21. An siRNA molecule that inhibits interaction of Survivin with hepatitis B X-interacting protein (HBXIP) by inhibiting expression of HBXIP, wherein the siRNA molecule comprises a sense strand encoded by a nucleic acid sequence as shown in SEQ ID NO: 7.

22. An siRNA molecule that inhibits interaction of Survivin with hepatitis B X-interacting protein (HBXIP) by inhibiting expression of HBXIP, wherein the siRNA molecule comprises an antisense strand encoded by a nucleic acid sequence as shown in SEQ ID NO: 8.

* * * * *